US009345413B2

(12) United States Patent
Schie et al.

(10) Patent No.: US 9,345,413 B2
(45) Date of Patent: May 24, 2016

(54) HEART RATE EXTRACTION USING NEURAL WAVELET ADAPTIVE GAIN CONTROL AND NEURAL PATTERN PROCESSING

(71) Applicants: David Schie, Cupertino, CA (US); Mike Ward, Tallmadge, OH (US)

(72) Inventors: David Schie, Cupertino, CA (US); Mike Ward, Tallmadge, OH (US)

( * ) Notice: Subject to any disclaimer, the term of this patent is extended or adjusted under 35 U.S.C. 154(b) by 209 days.

(21) Appl. No.: 13/964,923

(22) Filed: Aug. 12, 2013

(65) Prior Publication Data

US 2015/0045684 A1 Feb. 12, 2015

(51) Int. Cl.
*A61B 5/0452* (2006.01)
*A61B 5/04* (2006.01)
*A61B 5/00* (2006.01)
*A61B 5/0245* (2006.01)

(52) U.S. Cl.
CPC ............. *A61B 5/04017* (2013.01); *A61B 5/726* (2013.01); *A61B 5/7207* (2013.01); *A61B 5/7264* (2013.01); *A61B 5/0006* (2013.01); *A61B 5/0022* (2013.01); *A61B 5/0245* (2013.01); *A61B 5/0452* (2013.01)

(58) Field of Classification Search
CPC .. A61B 5/726; A61B 5/0452; A61B 5/04525; A61B 5/0468; A61B 5/04017; A61B 5/7207; A61B 5/7264
USPC .......................... 600/509, 515, 516, 517, 521
See application file for complete search history.

(56) References Cited

U.S. PATENT DOCUMENTS

2012/0123232 A1* 5/2012 Najarian ............. A61B 5/0022
600/345

* cited by examiner

*Primary Examiner* — Christopher D Koharski
*Assistant Examiner* — Michael Carey
(74) *Attorney, Agent, or Firm* — Weiss & Moy, P.C.; Jeffrey D. Moy

(57) ABSTRACT

An improved heart rate monitor is provided that can detect and distinguish a heartbeat from an otherwise contaminated system with noise components potentially larger than the signal of interest. Embodiments of the inventive monitor have an amplification system that eliminates large noise components so as not to saturate the system during detection of a desired low amplitude signal. In embodiments the elimination of noise components is accomplished through wavelet decomposition, and the removal of undesired components including interference components during adaptive gain control (AGC), in addition to hunting algorithms which minimize the error with techniques such as neural network least mean squares type back propagation algorithms.

20 Claims, 17 Drawing Sheets

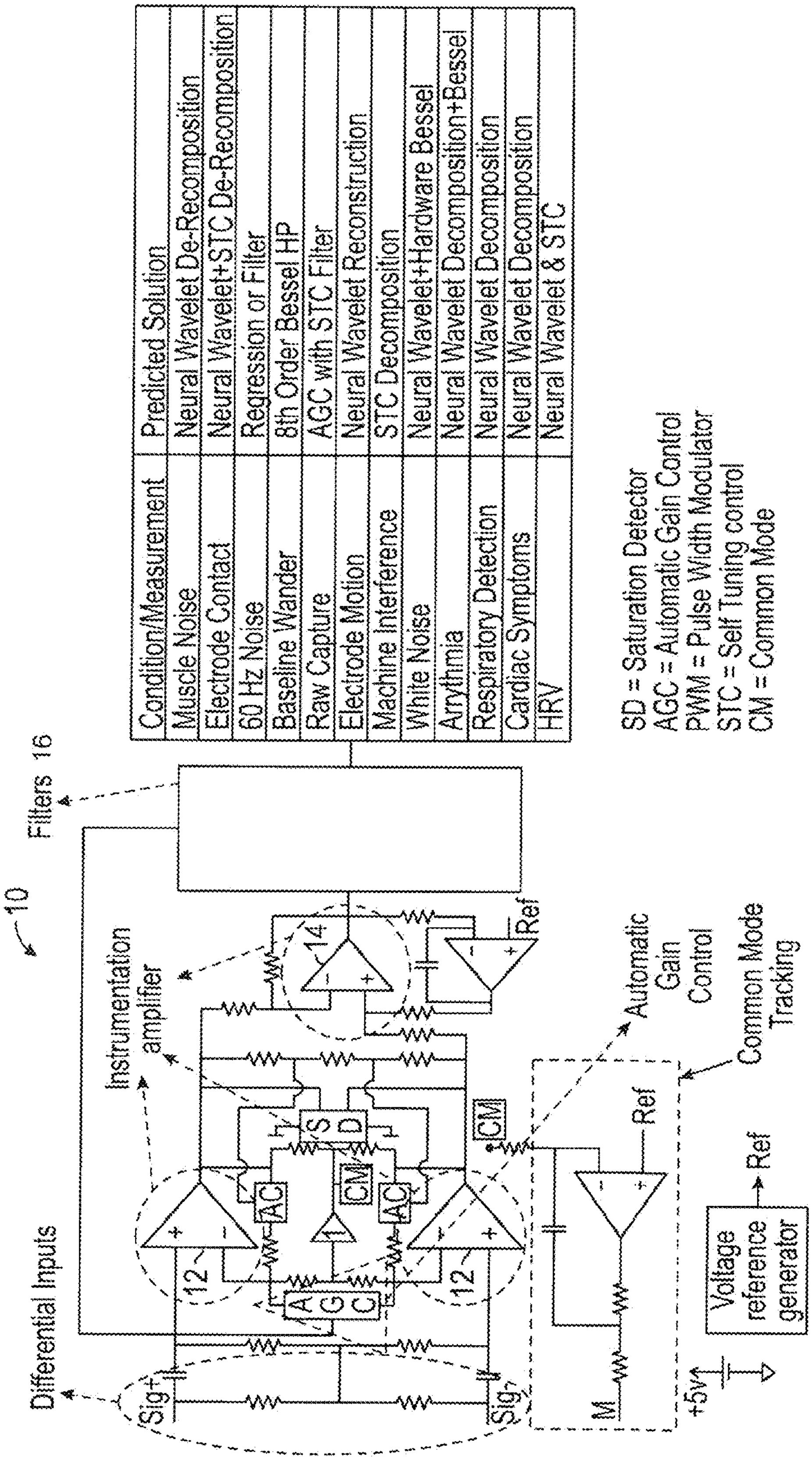

| Condition/Measurement | Predicted Solution |
|---|---|
| Muscle Noise | Neural Wavelet De-Recomposition |
| Electrode Contact | Neural Wavelet+STC De-Recomposition |
| 60 Hz Noise | Regression or Filter |
| Baseline Wander | 8th Order Bessel HP |
| Raw Capture | AGC with STC Filter |
| Electrode Motion | Neural Wavelet Reconstruction |
| Machine Interference | STC Decomposition |
| White Noise | Neural Wavelet+Hardware Bessel |
| Arrythmia | Neural Wavelet Decomposition+Bessel |
| Respiratory Detection | Neural Wavelet Decomposition |
| Cardiac Symptoms | Neural Wavelet Decomposition |
| HRV | Neural Wavelet & STC |

FIG. 1

Wavelet function
Ψ(*t*)

Shifted wavelet function
Ψ(*t-k*)

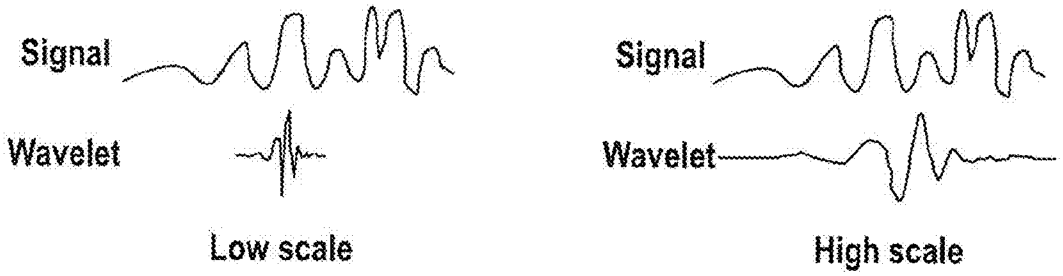
FIG. 17A
FIG. 17B
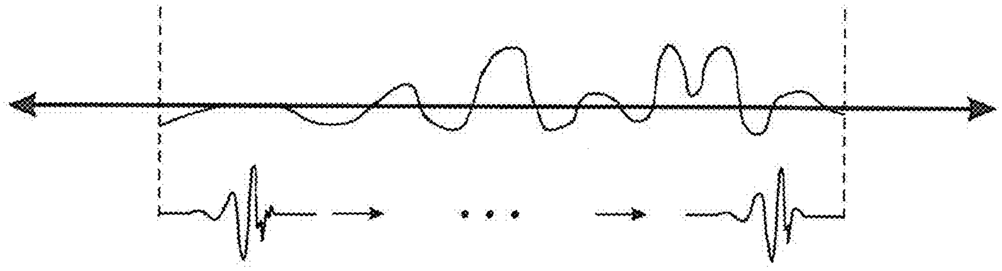
FIG. 18
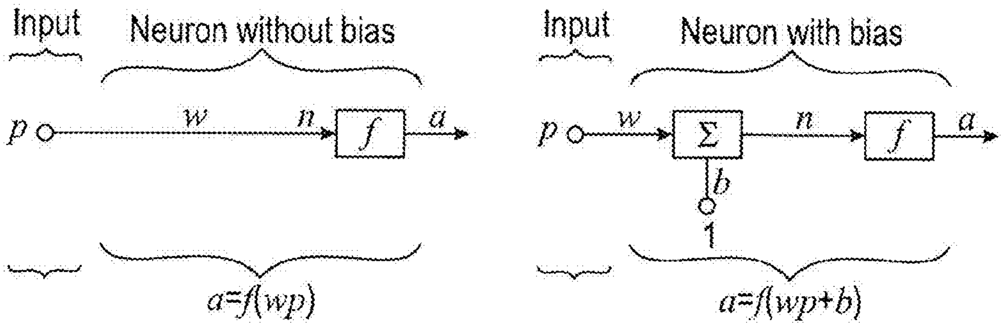
FIG. 19

Log-Sigmoid Transfer Function

HEART RATE EXTRACTION USING NEURAL WAVELET ADAPTIVE GAIN CONTROL AND NEURAL PATTERN PROCESSING

CROSS-REFERENCE TO RELATED APPLICATION

This application claims priority of U.S. Provisional Patent Application Ser. No. 61/682,271 filed Aug. 12, 2012, which is incorporated herein by reference.

FIELD OF THE INVENTION

The present invention in general relates to heart rate monitors, and more particularly, to a heart rate monitor that can detect and distinguish a heartbeat from an otherwise contaminated system with noise components potentially larger than the signal of interest.

BACKGROUND OF THE INVENTION

Heart rate monitors are popular in fitness and other applications which require the monitors to have size and form factors which do not interfere with the activity of the user being monitored. Unfortunately devices which measure heart rate presently require electrodes on multiple parts of the body, or a location near the heart on the chest, and are cumbersome, especially for women. Furthermore, heart rate signals on the arm are extremely small and require amplification, and the amplifiers may be easily saturated by interference components such as muscle movement, 60 Hz noise radiation from lighting or other equipment, respiration, electrode connection and disconnection during activity, baseline wander, or other sources of interference.

Thus, there exists a need for an improved heart rate monitor that can detect and distinguish a heartbeat from an otherwise contaminated system with noise components potentially larger than the signal of interest (and/or in the same frequency band), and to create an amplification system which can eliminate these larger components so as not to saturate the monitoring device.

SUMMARY OF THE INVENTION

An improved heart rate monitor is provided that can detect and distinguish a heartbeat from an otherwise contaminated system with noise components potentially larger than the signal of interest (and/or in the same frequency band). Embodiments of the inventive monitor have an amplification system that eliminates large noise components so as not to saturate the system during detection of a desired low amplitude signal. In embodiments the elimination of noise components is accomplished through wavelet decomposition, and the removal of undesired components including interference components during adaptive gain control (AGC), in addition to hunting algorithms which minimize the error with techniques such as neural network least mean squares type back (and/or feedforward) propagation algorithms.

Embodiments of the inventive heart rate monitor provide a method that improves correlation with a wavelet by creating a unique wavelet family which resonates specifically with the PQRST (P wave, QRS complex, T wave, where P wave represents atrial depolarization, QRS represents ventricular depolarization, and T wave reflects the phase of rapid repolarization of the ventricles) components of a basic electrocardiogram (ECG), but which otherwise follows the rigorous mathematical conditions for a wavelet including stability. In embodiments, wavelet decomposition is used in conjunction with a feedback network around the input stage amplifiers, which may be an analog or digital feedback network, to eliminate wavelet components which are caused by interference components, and which otherwise might saturate the detection system.

Embodiments of the present invention capture a signal utilizing a high common-mode rejection ratio (CMRR) termination, which does not include a DC path or load the probes. Additionally in embodiments, an instrumentation amplifier is broken into several parts which include an optional common mode driver, common mode accelerator, and an active feedback network, which could be an analog feedback network or a digital feedback network. An electronically controlled variable resistor on the input stage to the amplifier allows the gain of the system to be altered by the AGC algorithm, while an analog or digital feedback network around the input amplifiers allows decomposition and removal of unwanted signals that might otherwise saturate the detector.

In embodiments, a saturation detector, which can accelerate the time constant of the system, allows the system to recover quickly from saturated conditions if they do occur. Circuitry to create the common mode may optionally be buffered to drive an electrode, which drives the subject to a potential between the placement of the two differential input electrodes, which are placed over the skin far enough away to allow sufficient impedance for a differential measurement. The common mode driving circuitry has a low enough current (typically <10 mA) to ensure it does not create discomfort in a user being monitored.

In embodiments, the output of the common mode driving circuitry goes to a hardware low pass filter, such as a high order Bessel function, to remove components above the frequencies of interest. The result is then passed to a computing engine and passed through a high pass Bessel function, such as an 8th order Bessel function, to remove low frequency components not already removed by the terminator or AC transfer function within the INA. If the system is a portable system, the computing engine may be located in the cloud, or a remote server or computing device, while a portable device sends the results from the low pass Bessel filter, which can be implemented in hardware along with the terminator and AGC, either wirelessly or by storing it on a memory card such as an secure digital (SD) memory card for processing on a more powerful server or computing device.

BRIEF DESCRIPTION OF THE DRAWINGS

The subject matter that is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

FIG. 1 shows a circuit schematic of a heart rate monitor according to an embodiment of the invention;

FIGS. 17A and 17B illustrates the concept of taking a wavelet from its smallest scale to a scale which could be as large as the entire waveform being analyzed;

FIG. 18 illustrates a single line of the 3-D patterns of 9A and 9B (here color are the third dimensions but a z-axis could also be used) where a single level of scaling is translated across the waveform;

FIG. 19 shows a neural network neuron;

DESCRIPTION OF THE INVENTION

Figure 2:
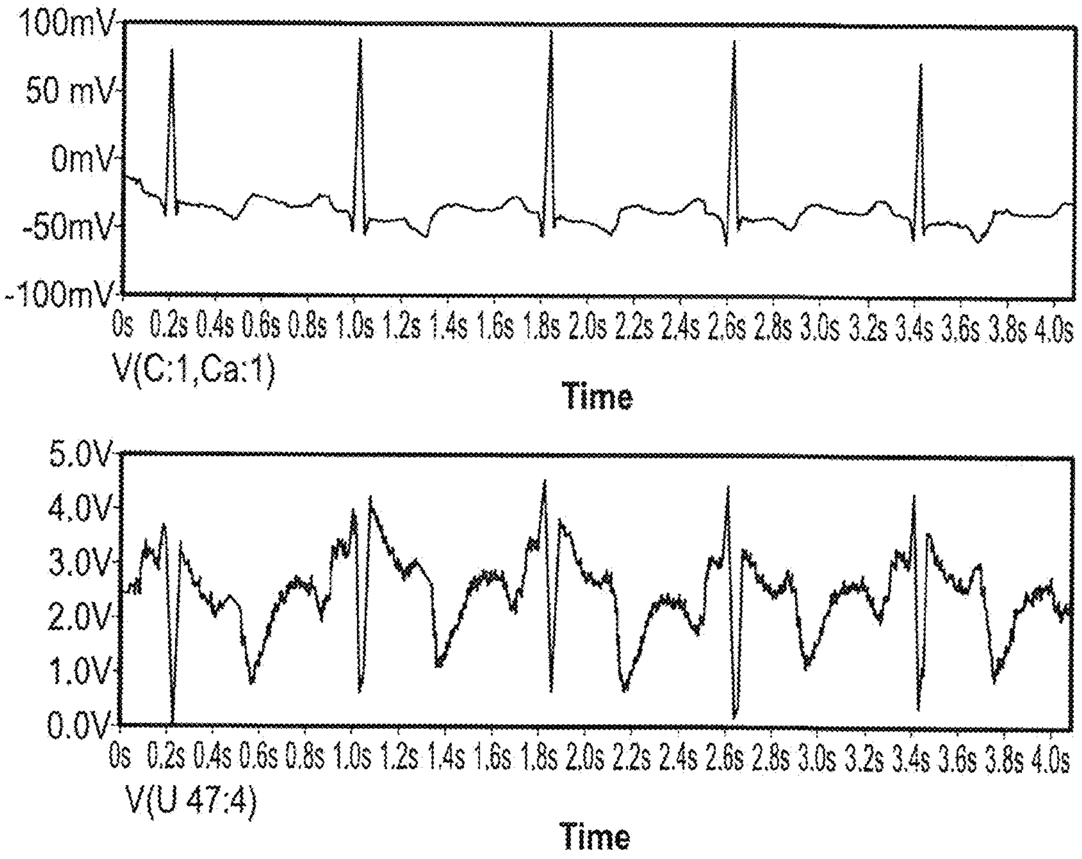
FIG. 2 (top) illustrates an amplified clean heart rate signal while (bottom) illustrates a filtered version of the same waveform.

An improved heart rate monitor is provided that can detect and distinguish a heartbeat from an otherwise contaminated system with noise components potentially larger than the signal of interest (and potentially with components in the same frequency band). Embodiments of the heart rate measurement device may be a portable apparatus ran by a battery. Embodiments of the inventive monitor have an amplification system that eliminates large noise components so as not to saturate the system during detection of a desired low amplitude signal. In embodiments the elimination of noise components is accomplished through wavelet decomposition, and/or the removal of undesired components including interference components during adaptive gain control (AGC), in addition to hunting algorithms which minimize the error with techniques such as neural network least mean squares type back (and/or forward) propagation algorithms.

Embodiments of the inventive heart rate monitor provide a method that improves correlation with a wavelet by creating a unique wavelet family which resonates specifically with the PQRST (P wave, QRS complex, T wave, where P wave represents atrial depolarization, QRS represents ventricular depolarization, and T wave reflects the phase of rapid repolarization of the ventricles) components of a basic electrocardiogram (ECG), but which otherwise follows the rigorous mathematical conditions for a wavelet including stability. In embodiments, wavelet decomposition is used in conjunction with a feedback network around the input stage amplifiers, which may be an analog or digital feedback network, to eliminate wavelet components winch are caused by interference components, and which otherwise might saturate the detection system. In embodiments the wavelet is configured to meet the following: transform and inverse transform and decomposition requirements; admissibility requirements including meeting the Perceval theorem condition; and convergence admissibility conditions, all of which will be discussed further below.

Embodiments of the present invention capture a signal utilizing a high common-mode rejection ratio (CMRR) termination, which does not include a DC path or overload the probes. Additionally in embodiments, an instrumentation amplifier includes an optional common mode driver, common mode accelerator, an active feedback network and or replacement of the input amplifiers or output summing amplifier with a transfer function, which could be an analog network or a digital, network. For example an electronically controlled variable resistor on the input stage to the amplifier allows the gain of the system to be altered by the AGC algorithm, while an analog or digital feedback network around the input amplifiers (such as an integrator) allows decomposition and removal of unwanted signals (such as DC offset) that might otherwise saturate the detector. The input amplifiers might be replaced with transfer functions of greater complexity which could include wavelet decompositions allowing only gained up components of interests through to the summer;

In embodiments, a saturation detector, which can accelerate the time constant of the system, allows the system to recover quickly from saturated conditions if they do occur. Circuitry to create the common mode may optionally be buffered to drive an electrode, which drives the subject to a potential between the placement of the two differential input electrodes, which are placed over the skin far enough away to allow sufficient impedance for a differential measurement. The common mode driving circuitry has a low enough current (typically <10 mA) to ensure it does not create discomfort in a user being monitored.

In embodiments, the output of the common mode driving circuitry goes to a hardware low pass filter, such as a high order low pass Bessel function, to remove components below the frequencies of interest. The result is then passed to a computing engine and passed through a high pass Bessel function, such as an 8th order Bessel function, to remove low frequency components. If the system is a portable system, the computing engine may be located in the cloud, or a remote server or computing device, while a portable device sends the results from the low pass Bessel filter, which can be implemented in hardware along with the terminator and AGC, either wirelessly or by storing it on a memory card such as an secure digital (SD) memory card for processing on a more powerful server or computing device.

Referring now to the figures. FIG. 1 shows a circuit schematic of a heart rate monitor 10 according to an embodiment of the invention. Sig+ and Sig− are signals originating from electrodes coupled to a subject's skin far enough away from each other to allow a signal in the pV or more range to be read by the inventive monitoring circuit. The signal goes into a terminator with high CMRR (127 db) which does not load the electrodes or include a DC path to ground which diminishes CMRR. This signal goes directly into the two input amplifiers 12 of the system. These two input amplifiers 12 in addition to the output summing amplifier 34 represent the instrumentation amplifier (it is known to those skilled in the art that a summing amplifier may include inverted or negative inputs to create a combination of sums and differences). An electronically controllable variable resistor sets the gain current used by the operational amplifiers and thus sets the gain. The boxes labeled AC are the feedback components. In an embodiment only AC components are allowed through. From example if an integrator were used as the feedback components then a s/(1+sTau) filter is created. The terminator then could be removed if a lower CMRR is acceptable. There is a stability restriction, however, to controlling only the AC feedback components. Therefore, in an alternative embodiment, the AC blocks and input stage amplifiers are replaced by digital filters (transfer functions) or transfer function creating networks such as neural networks which may include a more complex filter or which does wavelet decomposition and outputs a combination of selected decomposed wavelets which have been stripped of unwanted parts of the digitally decomposed wavelet but maintain stability. The filtered (including optional gain) AC components alone or in conjunction with the resistor setting the current between input amplifiers (if included) allow an adaptive gain control (AGC) to control amplitude although the AGC may be extended to control the inclusion or removal and gain of specific wavelet decomposition coefficients such that the input amplifiers 12 will only amplify that part of the signal of interest, while eliminating the potentially much larger amplitude interference components such as a wearer's muscle noise, electrode contact variations, 60 Hz noise, baseline wander, electrode motion, machine interference, white noise, arrhythmia, respiratory interference, cardiac symptoms or heart rate variability. Removing the unwanted components in this way at the input amplifiers of the INA has not been taught before and reduces the probability of saturation and/or the resolution of downstream components (for example if a large amplitude noise components were present and the AGC had to "zoom out" to accommodate it then the resolution of the downstream processors would need to increase to "see" the small heart rate waveform buried within the zoomed out waveform after post processing stripped out the noise component). Note that the AGC may also be designed to allow rather than remove through certain components such as arrhythmia, respiratory data, cardiac symptoms, heart rate variability or other waveforms in applications where the presence of such components is desired.

In embodiments, a thresholding algorithm utilizes an error minimization algorithm, such as least mean squares, to iteratively hunt or follow an error minimation contour to produce an optimal wavelet correlation to a train of heart beats. The thresholding algorithm decomposes a set of 2^n wavelet coefficients and removes any components of a set of signals which saturate the instrumentation amplifier and/or which are unrelated to the heart rate signal by thresholding only relevant wavelet coefficients from the wavelet in the path of the digital filter, where the removed or minimized components may include 60 Hz noise, muscle movement, electrode connection and misconnection, electromagnetic machine noise, respiration, motion artifacts, or other interference sources.

In an embodiment the instrumentation amplifier is configured for baseline capture by changing a set of feedback components such that saturation recovery is accelerated. In embodiments the baseline capture (CMRR improvement) may also be obtained with a third electrode driven to create a PI loop with a baseline reference being the potential mid-way between the set of signals (Sig+ and Sig−) from two electrodes placed a minimum distance but reasonable impedance from practical measurement away from each other (a few tens of k's of impedance). In embodiments the two or three electrodes are entirely located on an arm, chest, or leg of the subject. In embodiments, the electrodes are dry electrodes or wet electrodes such as red dot electrodes.

Continuing with FIG. 1, the output of the differential input amplifiers 12 is summed and gained by the final output amplifier 14, and fed into filters 16. The boxes SD in FIG. 1 are saturation detectors which accelerate the time constant of the system if the amplifier does saturate, and then release when the common mode recovers. The CM box labels the common mode which is halfway between the outputs of the two input amplifiers 12, and which can optionally be buffered by the integrator with output M which is connected to a third electrode preferably placed halfway between the two differential electrodes connected to the patient. The output filters are then fed to an extraction engine indicated in the table which utilizes neural networks, wavelets and other STC or self tuning control methods to extract the waveform. This engine may also provide information to the AGC and/or AC blocks and/or AC block/input amplifier replaced transfer functions to optimize the components allowed through the first stage of the INA. This would be in addition to any wavelet, neural network or STC optimization which could be done at in the first stage of the INA. In one embodiment, however, the AGC could be only a potentiometer, the AC an integrator to remove DC and low frequency components and high frequency components (s/(1+sTau) type response), and all extraction done per the pattern recognition taught in this application done post INA output.

Figure 3:
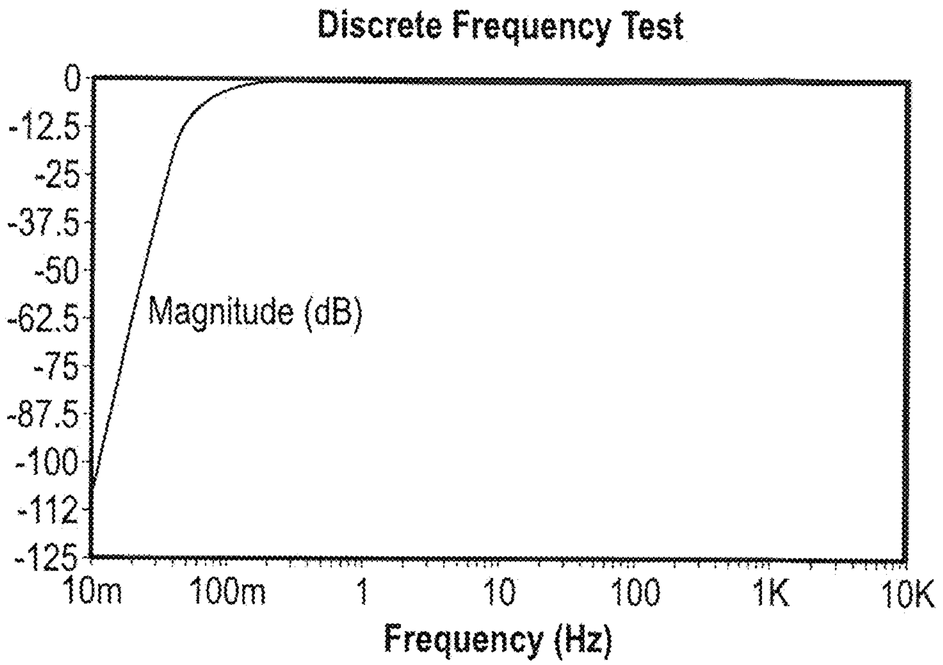
FIG. 3 shows the discrete gain transfer function for a high pass Bessel function.
Figure 4:
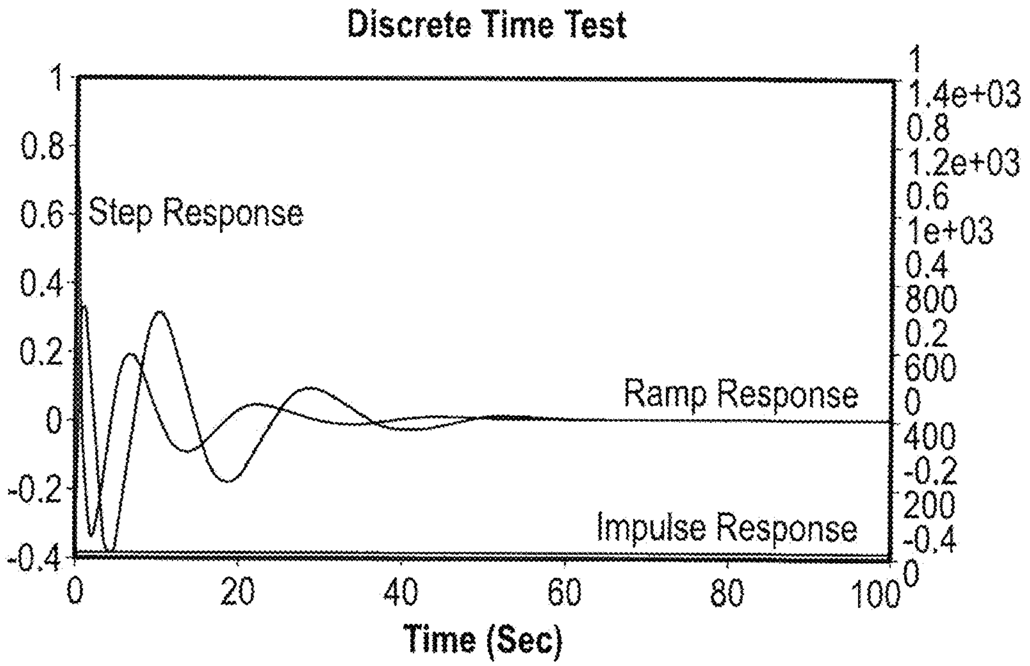
FIG. 4 shows the highpass impulse response of an $8^{th}$ order high pass Bessel function.

FIG. 2 shows a "clean" heart rate amplified waveform, while the lower figure shows the same waveform including the effects of filtering;

FIG. 3 shows the discrete transfer function for an $8^{th}$ order high pass Bessel function used in embodiments of the invention. In embodiments, the $8^{th}$ order Bessel function digital filter is contained in the primary processing computer. This may be the microcontroller which also does the adaptive gain control, however, it may also be a separate computing engine located in the cloud to reduce the computational requirements and power consumption of the portable device which otherwise could use a lower end microcontroller or digital signal processor (DSP). FIG. 4 shows the impulse response of the highpass $8^{th}$ order high pass Bessel function.

Figure 5:
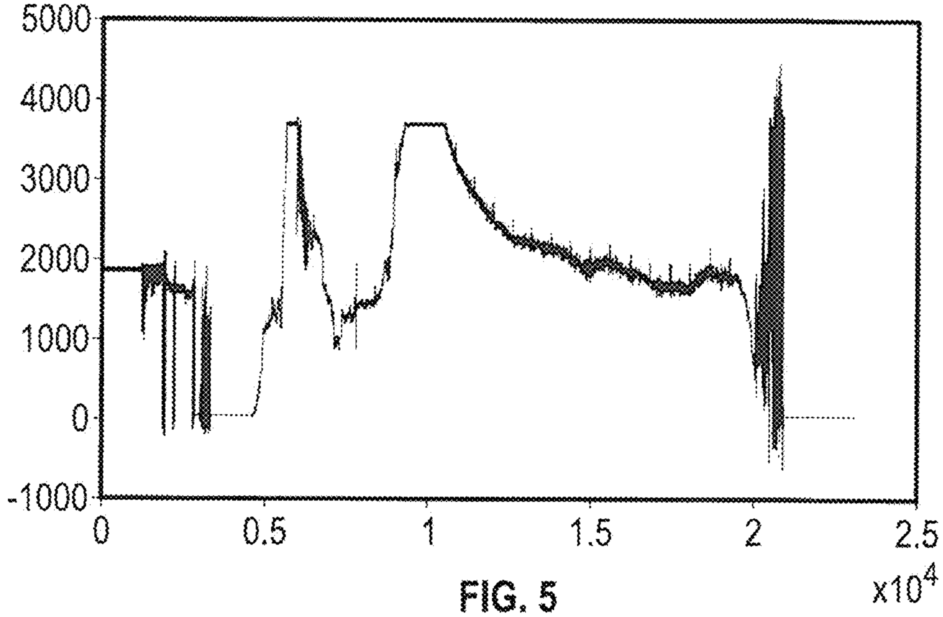
FIG. 5 shows raw data that might be provided to the AGC or terminator (if used) from differential electrodes.
Figure 6:
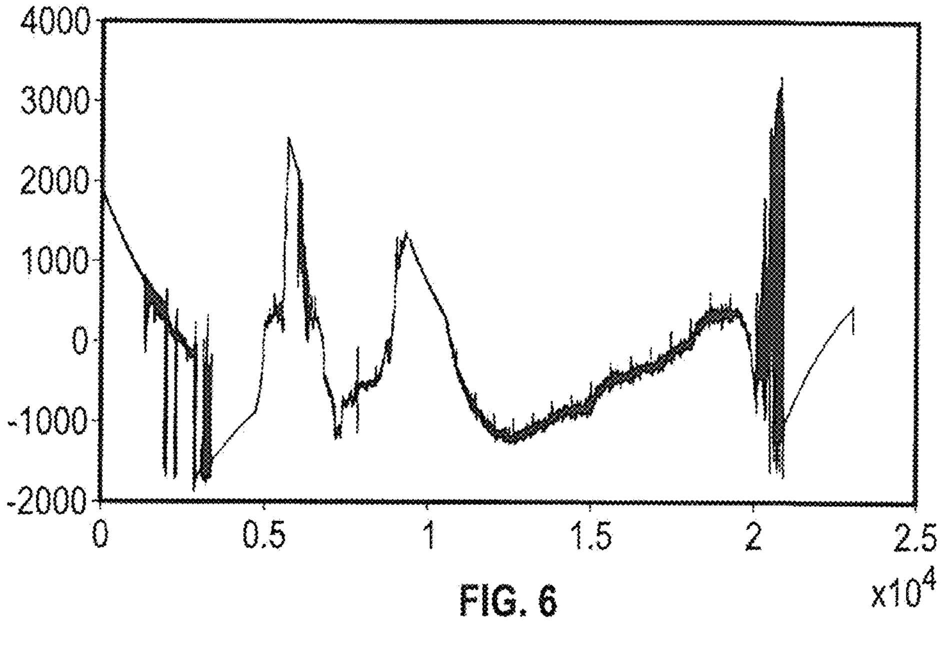
FIG. 6 shows the waveform in FIG. 5 filtered by a high order Bessel function.
Figure 7:
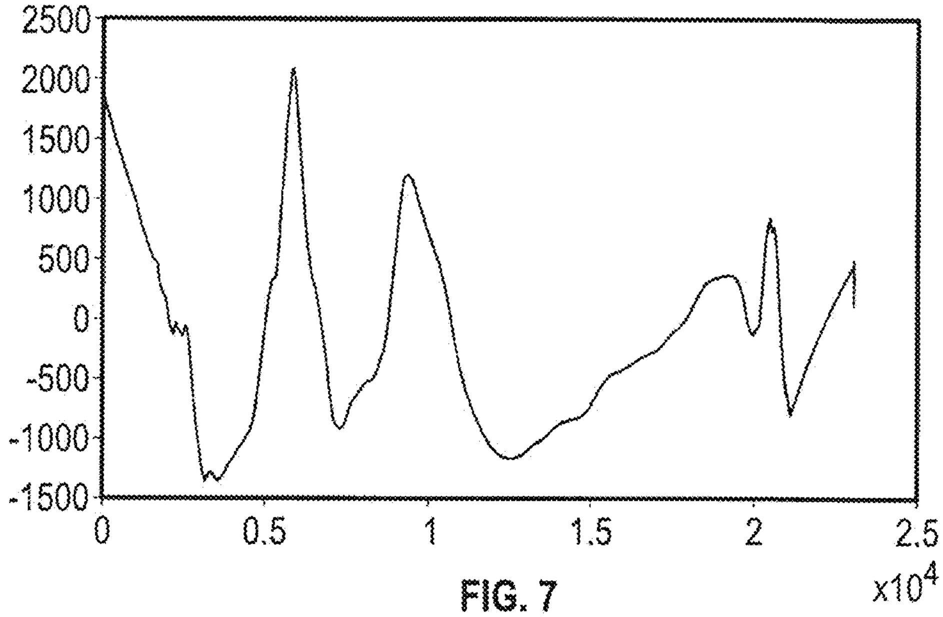
FIG. 7 illustrates the waveform in FIG. 6 after an averaging (smoothing) routine which averages each point by the 150 points around it to provide a smoothing effect.
Figure 8:
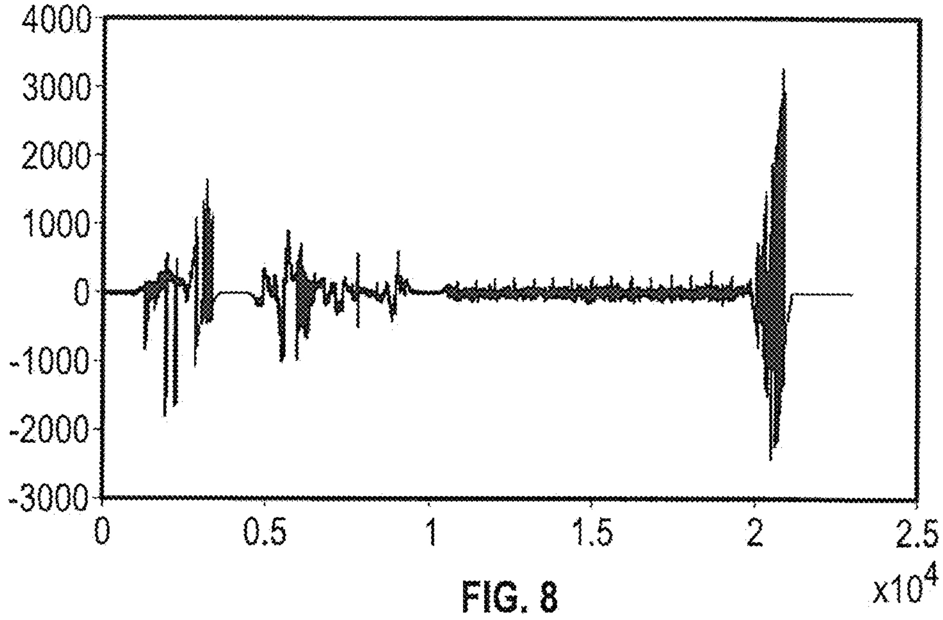
FIG. 8 shows the waveform of FIG. 6 after the waveform of FIG. 7 is subtracted from it.

FIGS. 5-9B illustrate an example case for several seconds of heart rate data. The waveform of FIG. 5 represents the noisy input data from a highly mobile subject. The waveform includes the expected baseline wander, muscle interference, loss of signal as the electrodes connect and disconnect, 60 Hz powerline interference and other non-idealities. As a first step, a Bessel Filter, removing low frequency artifacts outside the heart rate window (higher frequency artifacts had already been removed by the hardware filter) is shown in FIG. 6. The waveform in FIG. 7 (step 2) is the result of averaging at each point, and the 150 points around that point, and produces the common mode which can be subtracted from the overall waveform in the next step. At step 3 the baseline in FIG. 7 is subtracted from the filtered waveform of FIG. 6 with the result as shown in FIG. 8. FIG. 8 shows the subject data with the baseline eliminated, and which is now "smooth" and much easier to work with.

Figure 9A:
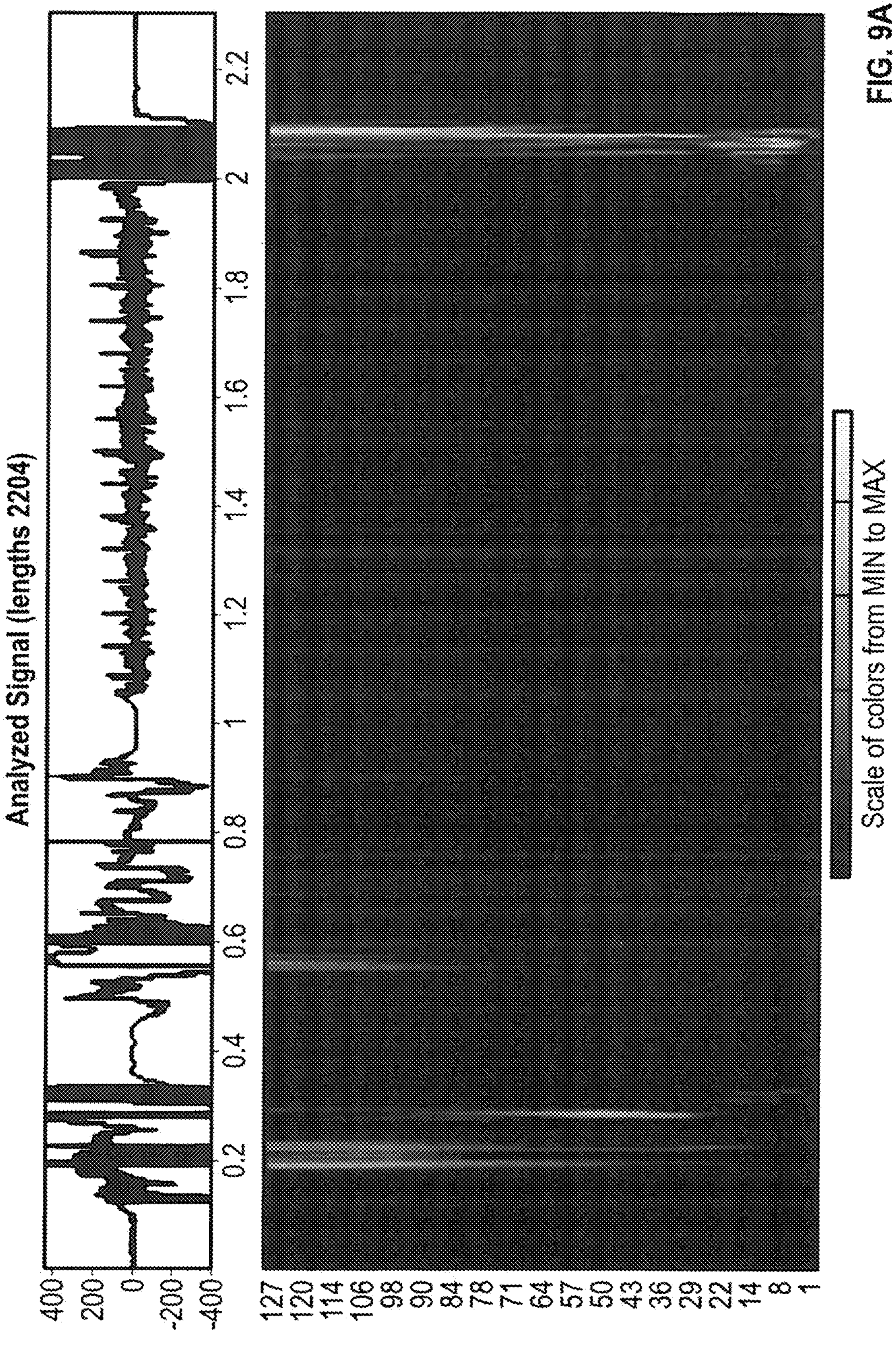
FIGS. 9A and 9B illustrates wavelet three dimensional pattern, image analysis of the waveform of FIG. 8 at different AGC settings (AGC is a pattern optimizing algorithm)
Figure 9B:
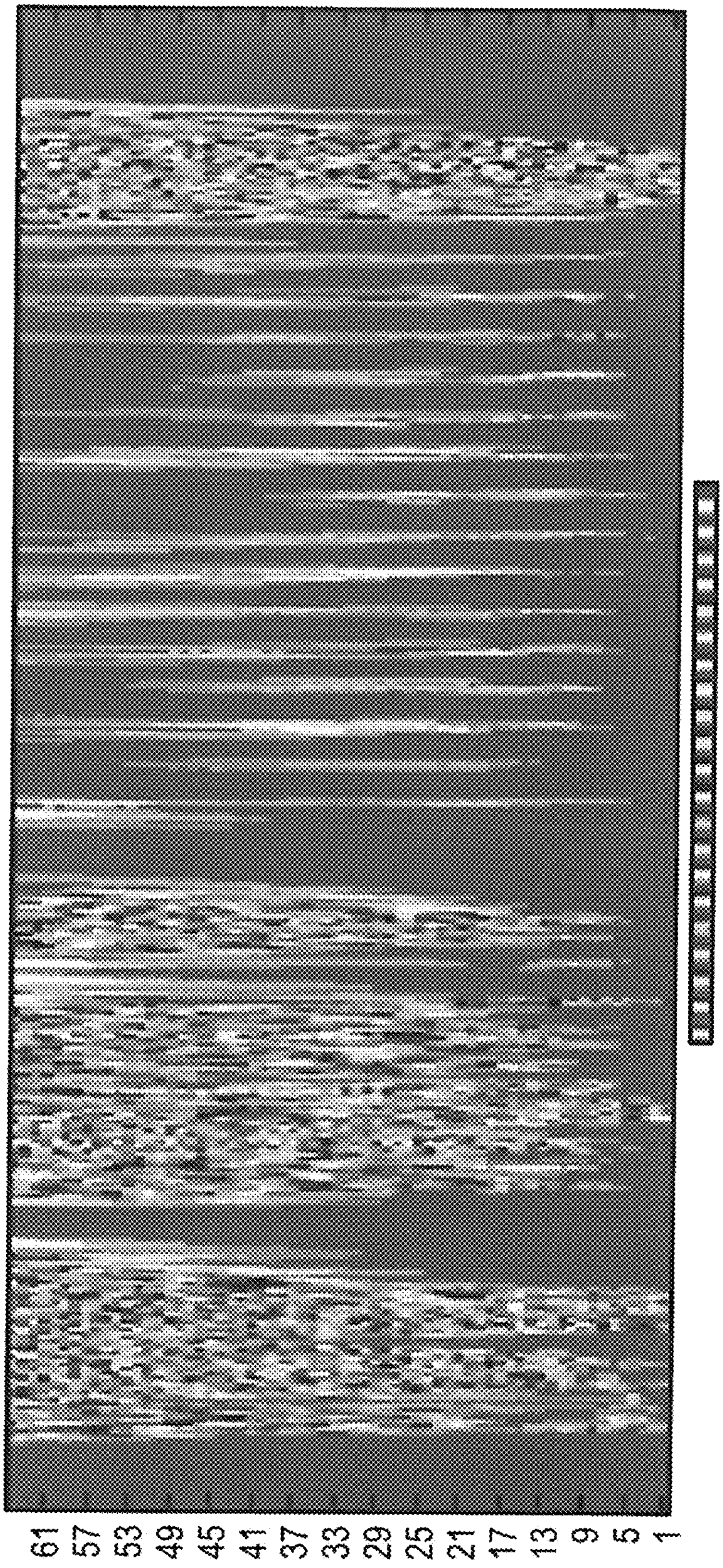

FIGS. 9A and 9B show a wavelet visualization in three dimensions of the wavelet correlation to the heart rate waveform of FIG. 8. Here the third dimensions is color but could just as easily be a z-axis. This visualization clearly shows the heart beats (FIGS. 9A and 9B) which are now much more easily discernible than they were in the original data. The 9A and 9B visualizations are shown to illustrate different pattern optimizations that the AGC algorithm could use to draw the heart wave relevant patterns out from the background noise. This type of AGC optimization may be further accomplished by training of a neural network. Specifically, by exposing the network to expected patterns for the heart rate in these types of plots allow the neural network to find groups of heart, beats and to predict the missing heart rates such that a heart rate can be continuously provided. It is noted that this pattern recognition neural network may be used either: i) for the AGC algorithm in the first stage of the INA, which is being used to optimize the waveform components being allowed through while stripping away unwanted signal components or those that might otherwise saturate the instrumentation amplifier or force a large zoom out of the waveform; or ii) as a post processing method to use image processing to identify heart beats within the waveform already amplified and filtered earlier;

At step 4, adaptive gain control (AGC) is performed on a signal using an iterative wavelet algorithm which decomposes the signal into an image. In general, the most difficult part of capturing a small signal hidden amongst noise within the spectrum of interest is developing an AGC routine that can optimize the hardware system gain for only the detected signals of interest. It is clear that neither conventional time nor frequency domain techniques (like amplitude or frequency capturing) will work since the frequencies of the interference are not distinct from the waveform of interest, and the noise, motion, and muscle artifacts may well be much larger than the amplitude of the waveforms of interest.

A solution for an AGC routine is found in a branch of mathematics called wavelets. Wavelets were invented to address the problem of correlating a signal with a general shape (like a QRS complex) to a noisy waveform hiding such signals such that the correlation may be used to identify and extract the desired signal. The difference between a wavelet analysis and a Fourier or continuous time analysis is that the wavelet is "spongy" in scale, frequency and translation, and as such can provide a correlation to a signal "hiding" within a very complex signal that otherwise would be meaningless.

The following is a brief overview of wavelets starting with a parallel but more common type of decomposition-fourier analysis.

A Fourier transform is defined by the following equation and graphically in FIG. 9 as a signal broken up into sinusoids of different frequencies.

$$F(\omega) = \int_{\infty}^{\infty} f(t)\, e^{-j\omega t} dt$$

By deconstructing a signal into constituent signals at different frequencies a corresponding signal spectrum may be created, and tools such as a spectrum analyzer may be used to analyze a signal. A signal that is repetitive has spectral content that is easy to discern in the frequency domain and to conduct a variety of filtering, AGC or signal processing functions upon. In addition the signal may be rebuilt with the function by re-combining the deconstructed signals. However, when the signal is not consistent and repetitive, and when the signals of interest are not distinct from the spectra that form the noise, how can we decompose it? Under this circumstance a spectrum analysis would be "dancing around" with varying amplitudes moving along the x-axis in a way which evades "normal steady state" frequency domain filtering and signal processing expectations. To solve this problem a wavelet transform is used with the following equation:

$$C(\text{scale, position}) = \int_{\infty}^{\infty} f(t)\psi(\text{scale, position}, t)dt$$

Figure 11:
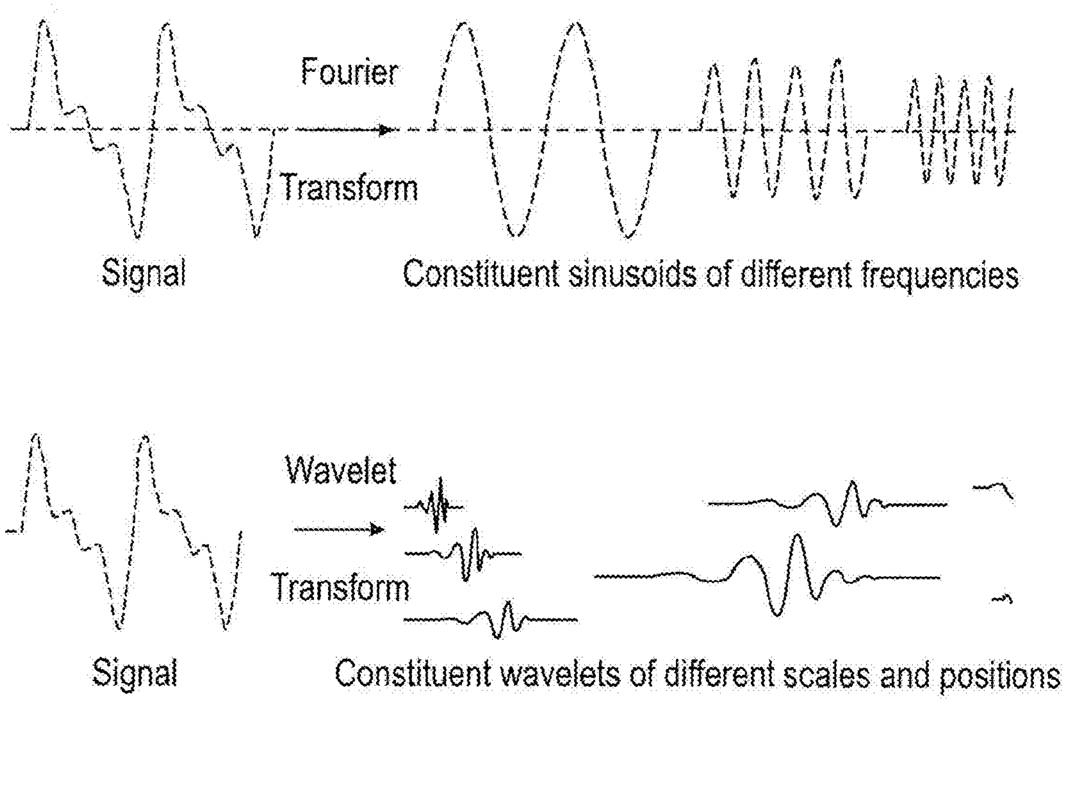
FIG. 11 (top) illustrates a fourier decomposition of a waveform into frequency components while (bottom) illustrates the same waveform broken into wavelet components. The fourier is presented as a parallel deconstruction to help the reader comprehend wavelets.

The wavelet transform is in some ways similar and is related to a Fourier transform but it goes further attempting to unlock the patterns of frequency, translation, and amplitude through the use of correlation coefficients. Interestingly, these correlation coefficients when applied to the deconstructed waveform (similar to the deconstruction of a signal into sine waves of different frequencies), completely defines the waveform and allows it to be rebuilt completely, just as with Fourier analysis, with no loss of data. FIG. 11 illustrates the components of a wavelet transform.

A wavelet function is a unique function with certain properties that make it useful for deconstruction of a signal. There are a number of different types of wavelets, and it is possible to create new wavelets. In an embodiment of the invention, a wavelet is carefully constructed to optimize the identification of the QRS complex for heart rates. This inventive wavelet is created by using two conditions: i) resonance with the P, QRS, T components of a typical heart beat; and ii) the mathematical conditions for a wavelet (described in Appendix A). The use of a wavelet specific to heart beats improves the correlation coefficients versus the use of other existing wavelets, speeding the identification process and reducing computational requirements.

Figure 10:
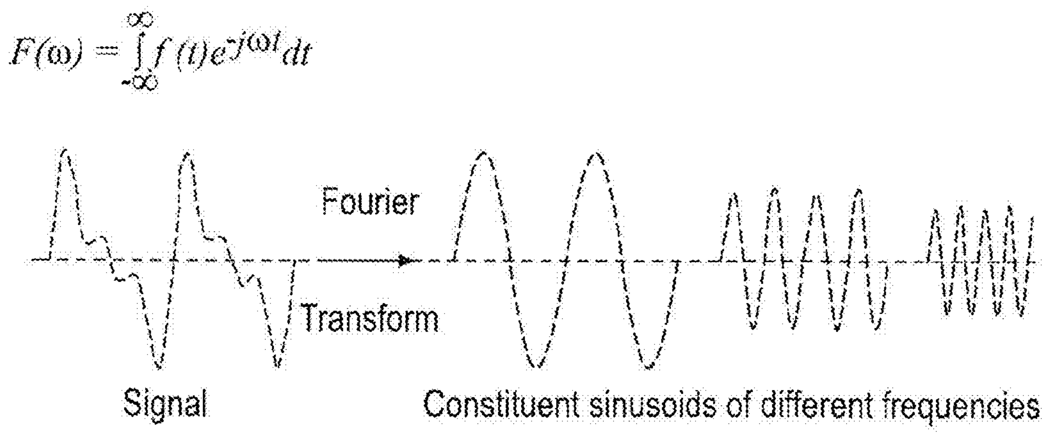
FIG. 10 illustrates a fourier decomposition of a waveform into frequency components to illustrate the concept of waveform deconstruction.
Figure 12:
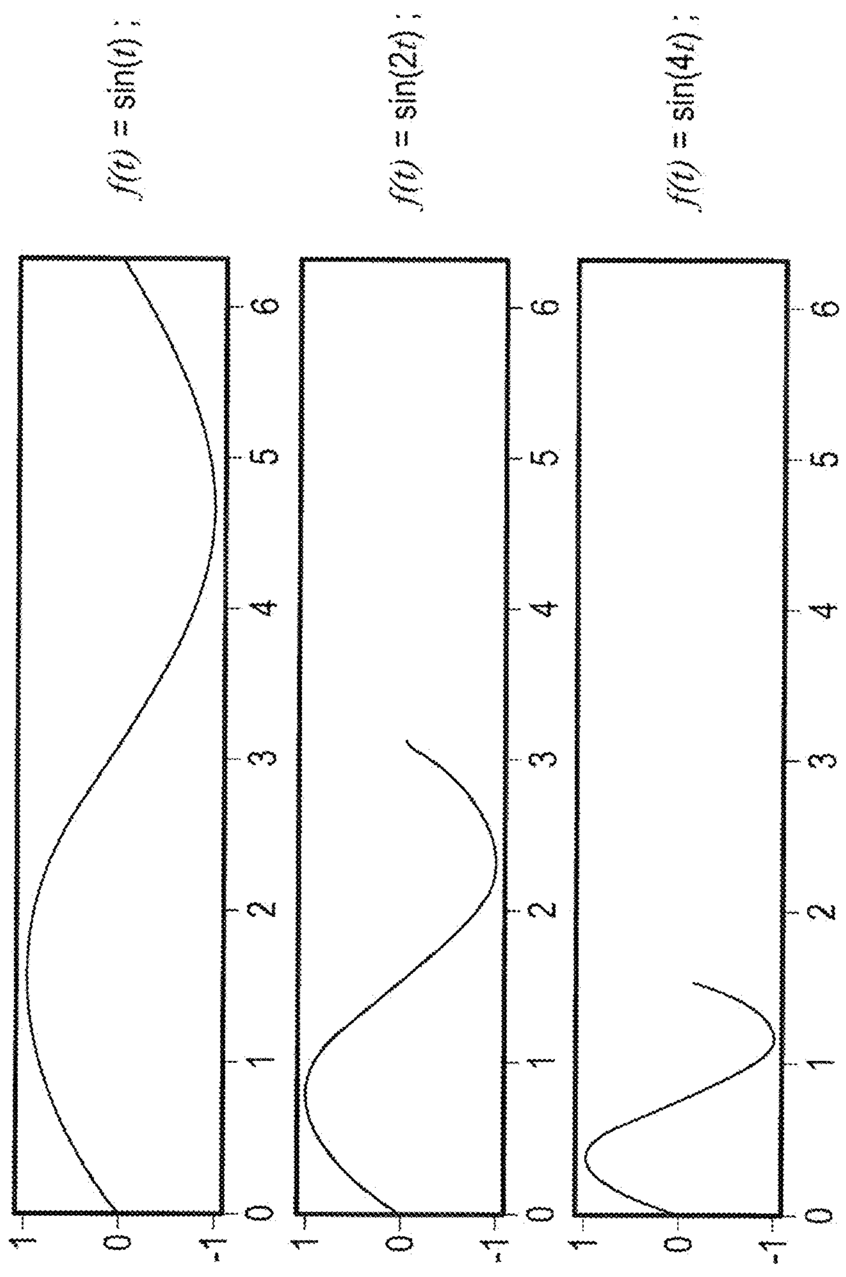
FIG. 12 illustrates the frequency scaling of fourier components.
Figure 13:
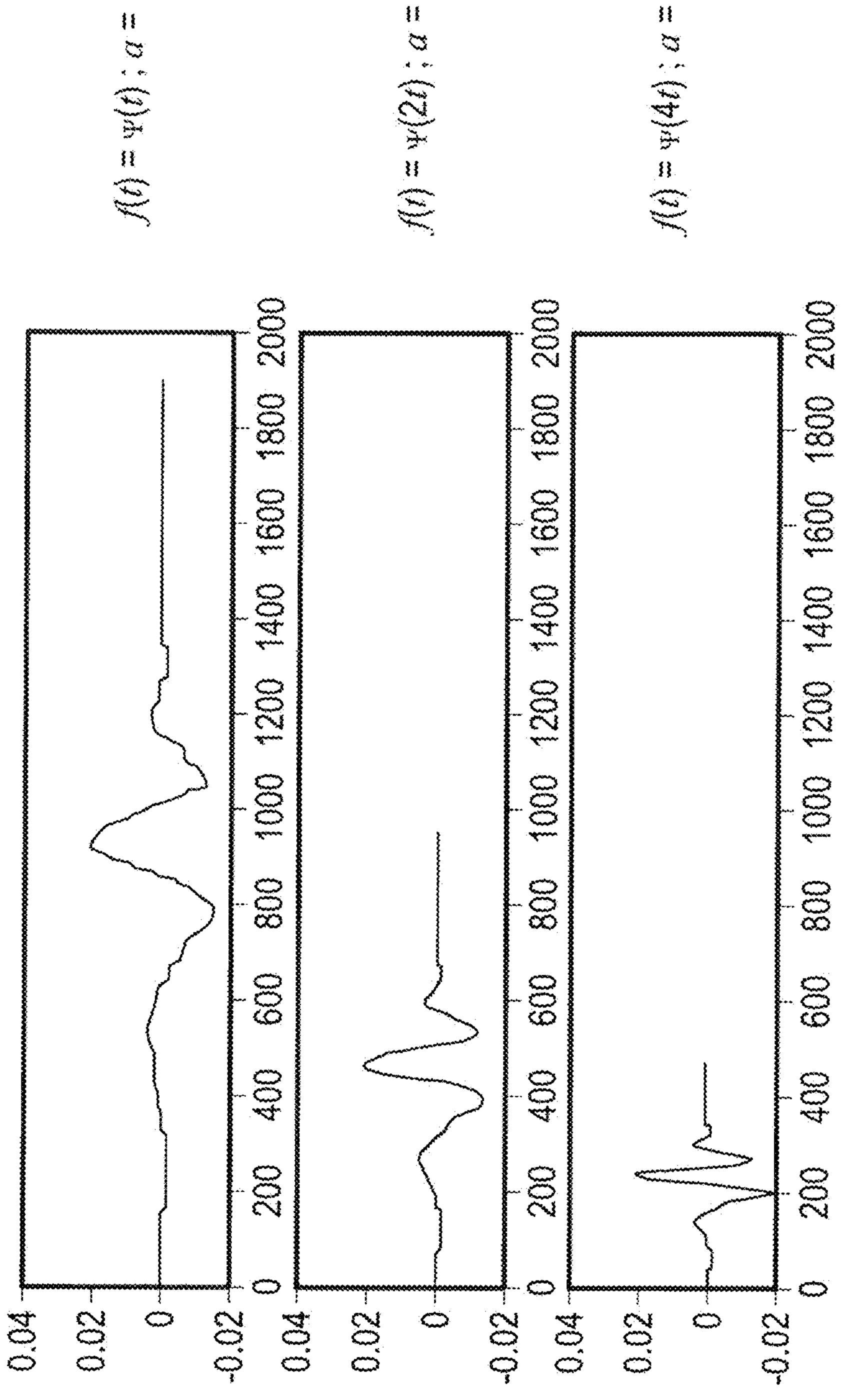
FIG. 13 illustrates the frequency scaling of wavelet components.
Figure 14A:
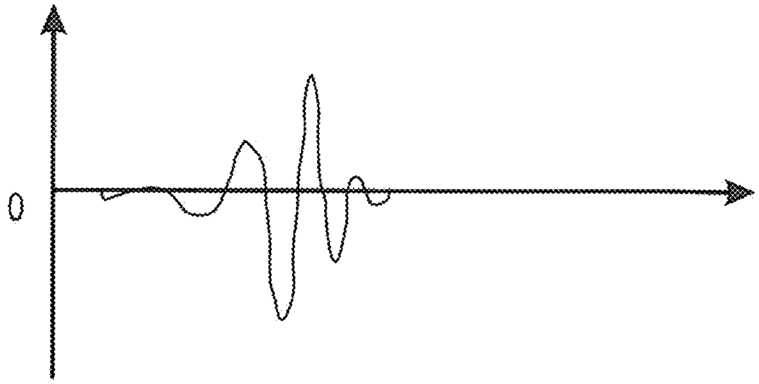
FIGS. 14A and 14B illustrate the wavelet concept of translation.
Figure 14B:
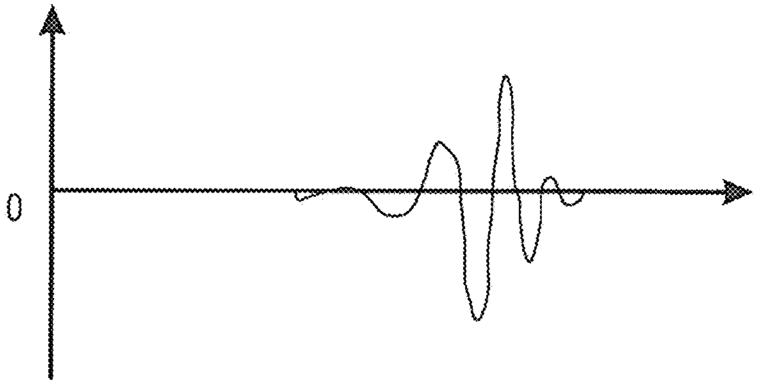

FIG. 10 illustrates the conventional breakdown of a waveform into its frequency components using well known Fourier analysis methods. Comparisons between Fourier analysis shown in FIG. 10 and the parallel breakdown of a waveform into its constituent parts using wavelet decomposition is shown in FIG. 11. In the Fourier case there is only amplitude and frequency variation to deconstruct the waveform. With wavelets there are scales and position deconstructions. A scale deeonstruction is as simple as it sounds, and involves scaling the wavelet. This is shown in FIG. 11 and in FIG. 13. FIG. 12 shows similar scaling as might be used in a Fourier analysis. In addition to decomposing a signal into scaled wavelets, the wavelets may be shifted across the signal of interest to determine the level of correlation as shown in FIG. 14A and FIG. 14B.

Figure 15A:
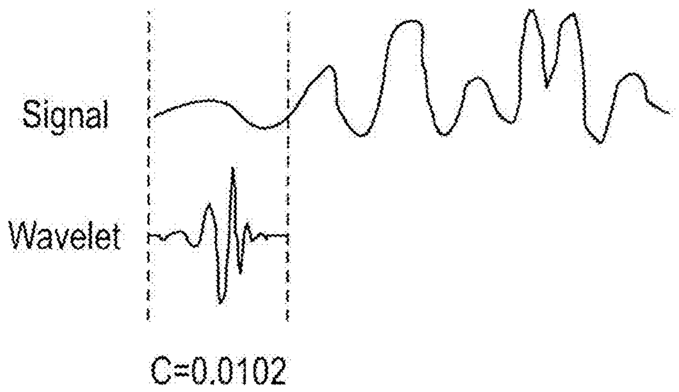
FIGS. 15A, 15B and 16 illustrate the concept of shifting scaled wavelets across a signal of interest to build up pattern images such as those shown in 9A and 9B.
Figure 15B:
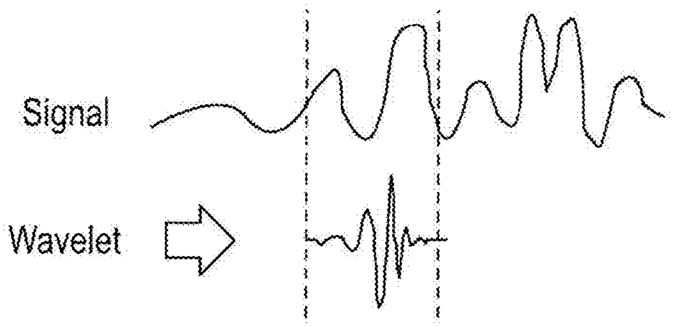
Figure 16:
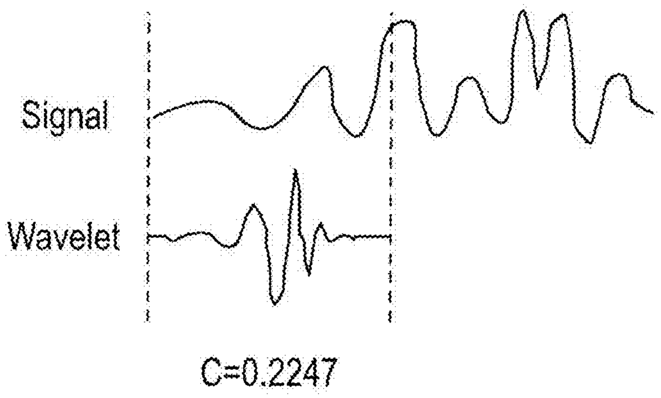
Figure 20:
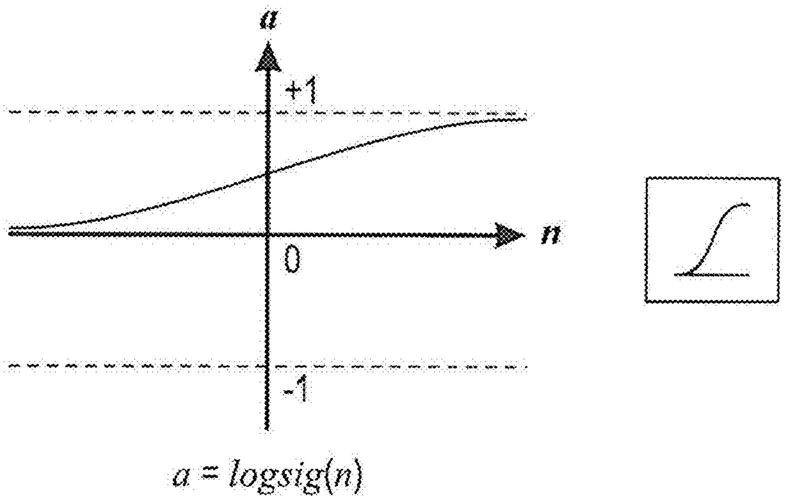
FIG. 20 shows a neuron decision function, in this case a log sig function.

In a wavelet analysis, a base wavelet is shifted across a signal of interest. At each "slice" a coefficient is calculated, which is an indicator of how well the wavelet matches that part of the waveform. If the signal and the wavelet were identical the correlation factor would be 1. If not it is some fraction which numerically represents how good the "match" is. The diagrams of FIGS. 15A, 15B and 16 illustrate how we translate the wavelet across the signal of interest. Once a wavelet of a certain scale has been translated across the entire waveform of interest, the correlation coefficients related thereto against time are stored, the wavelet is scaled and the process is repeated as shown in FIG. 18. Each line of the three dimensions patterns in FIGS. 9A and 9B are repeated translations across the waveform of interest with each row representing a different scale.

The scaling and subsequent translation of the wavelet across the waveform of interest produces a coefficient map with "pixels" with a grayscale between 0-1 which are an indication of how well the wavelet is matching each slice of the waveform with that scale. As shown in FIG. 17A, a wavelet may begin as a very small signal for the first row of the translation and then may be expanded until eventually it could be as large as the entire signal as illustrated in FIG. 17B. It is not necessary to calculate every scale and translation within a "pixel map", as described above since there is some knowledge of what a heart signal looks like, and some decisions can be made based on the limitations thereof and further some guidance is accrued as the "pixel map" starts to form in certain areas. For example, the scale of the wavelet may be limited to only those scales corresponding to the sample rate of the waveform since heart rate periods are well defined.

As shown earlier, FIGS. 9A and 9B are wavelet "pixel maps". In FIG. 9A, the (upper) box is a zoomed view of our waveform for analysis. The AGC determines the amount of gain determined iteratively based upon an algorithm which is "taught" some properties of the expected heart rate waveform, and thus has some idea where the signal is expected to be. It will move in and out based upon the strength of correlation of the wavelet coefficients, an error minimizing algorithm gradient based upon learned (trained) input vectors, and specific constraints. To better understand this consider 9A and 9B as different wavelet decompositions responding to an error minimizing algorithm: These two pattern visualizations both can be seen to highlight the heart rate waveforms, however, the optimization of certain parameters by the error minimizing algorithm (including but not limited to thresholding) produces more defined correlation factors for the group of waveforms from center to ⅞ of the waveform while over highlighting and washing out those components in the first and final $8^{th}$ of the analysis (viewing left to right). In the meanwhile algorithm 9A does not over highlight the first half and final $⅛^{th}$ components but produces far less distinct results in the mid to ⅞ sections of the analysis. In both of these visualizations, the y-axis is the scale factor of the wavelet (remember that as we move up and down the plot, the more "stretched" or "squeezed" the wavelet is). The x-axis is time, following the time domain of the subject signal. The colors represent the values of the correlation coefficients for each scaled "pixel" at each point in time. In fact these visualizations represent a color map of where a signal might be hiding, and a mere glance at either visualization brings out the heart rate from the otherwise difficult to analyze environment. The error minimization algorithm within the AGC or in the post process extraction engine may be used to alter the decompositions of interest, to change the thresholding, to call on additional optical pattern recognition transforms which are known to optimize contrast and resolution in other optical pattern recognition applications such as OCR or facial recognition, or to utilize other algorithms such as neural network clustering algorithms to draw together areas of interest to make them distinct. Some of these different algorithms are described in the table in FIG. 1 with the noise factors to which they provide the great level of help;

It is useful that even with the naked eye both visualizations very distinctly highlight the heart rate signals that even in the top box look like heart rate signals (the pronounced repetitive vertical spikes in regular succession). What is not quite so obvious is that the correlation coefficients even in the "noisy" areas are very clear to the appropriate algorithm, even though they are not as clear to an observer's eyes.

Even in the presence of heart rate variability, arrhythmia, or other non-idealities in the PQRST waveform, there is still some level of scales and translation that are pattern detectable by the right algorithm (more on this in a moment). Now consider that a lot is known about what a heart beat looks like, how quickly it can change (an example constraint), and where to look for it in the modified "intelligent pixel map" that is really being built to find heart rates. We can also use these clues and constraints to used to speed up the capture algorithm so that it quickly sets the appropriate AGC. Note that if for some reason the AGC needs to change—if the subject moves the sensor, it slips or changes for any reason—that the iterative AGC routine described above will immediately recognize the loss or change of signal and attempt to move in the direction which will improve or recapture the signal. If the signal is lost completely it will use certain rules of initial search which are taught to it and certain constraints to attempt to determine just where the heart beat is hiding yet again. Each time a learning AGC routine learns about its latest subject, however, recapturing the signal becomes easier and quicker. Once the AGC routine starts to see signs that the heart beat is likely to be there, it will utilize a number of techniques to hone in on the heart beat based on the "intelligent pixel map."

Next, consider analysis of the "intelligent pixel map", and how to make the system automatically optimize the AGC and hone in on the heart rate signal by helping it understand what a heart rate waveform should actually look like. To do this, it must be considered that in the example above, the data is not a complete set, and a "wild ride" can be expected as an attempt is made to maintain a bead on our elusive heart rate data.

To recognize patterns in our "intelligent pixel map" a neural network may be utilized. Neural networks are known to have an excellent ability to recognize patterns. Neural networks are used for example for optical character recognition or image processing. A neural network is a network made up of an input layer (a bunch of inputs) all tied to some internal layers through a weighting which is applied to a decision transform at each node, which are in turn tied either to more similar internal layers and/or to an output layer. It is known that if the neural network is "shown" an input which is supposed to correlate to a certain output, that it can be "trained" to weight those internal neurons such that any time the input is seen it will create or recognize the appropriate output. A unique property of the network is that if it sees a noisy image or something close to but not exactly what it expected, it will still output something close to the correct output, or can be constrained to make a probabilistic decision and output the most likely output. As such neural networks are excellent at classifying patterns. They also have the enviable property of being easily implemented in silicon in the analog realm without significant computing resources needed due to their recursive nature and small amount of analog memory use. The easiest way to illustrate the operation of our neural network, is to describe a network capable of recognizing the entire alphabet from a pixel matrix, even if the pixels are non-ideal and there is significant noise present.

Figure 21:
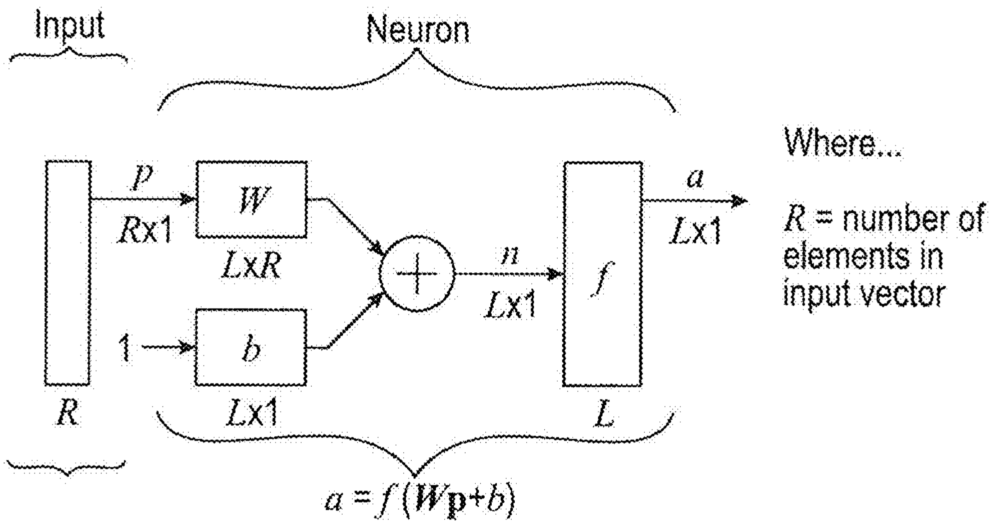
FIG. 21 shows an input layer applied to a multiplicity of neurons and in turn to an output.
Figure 22:
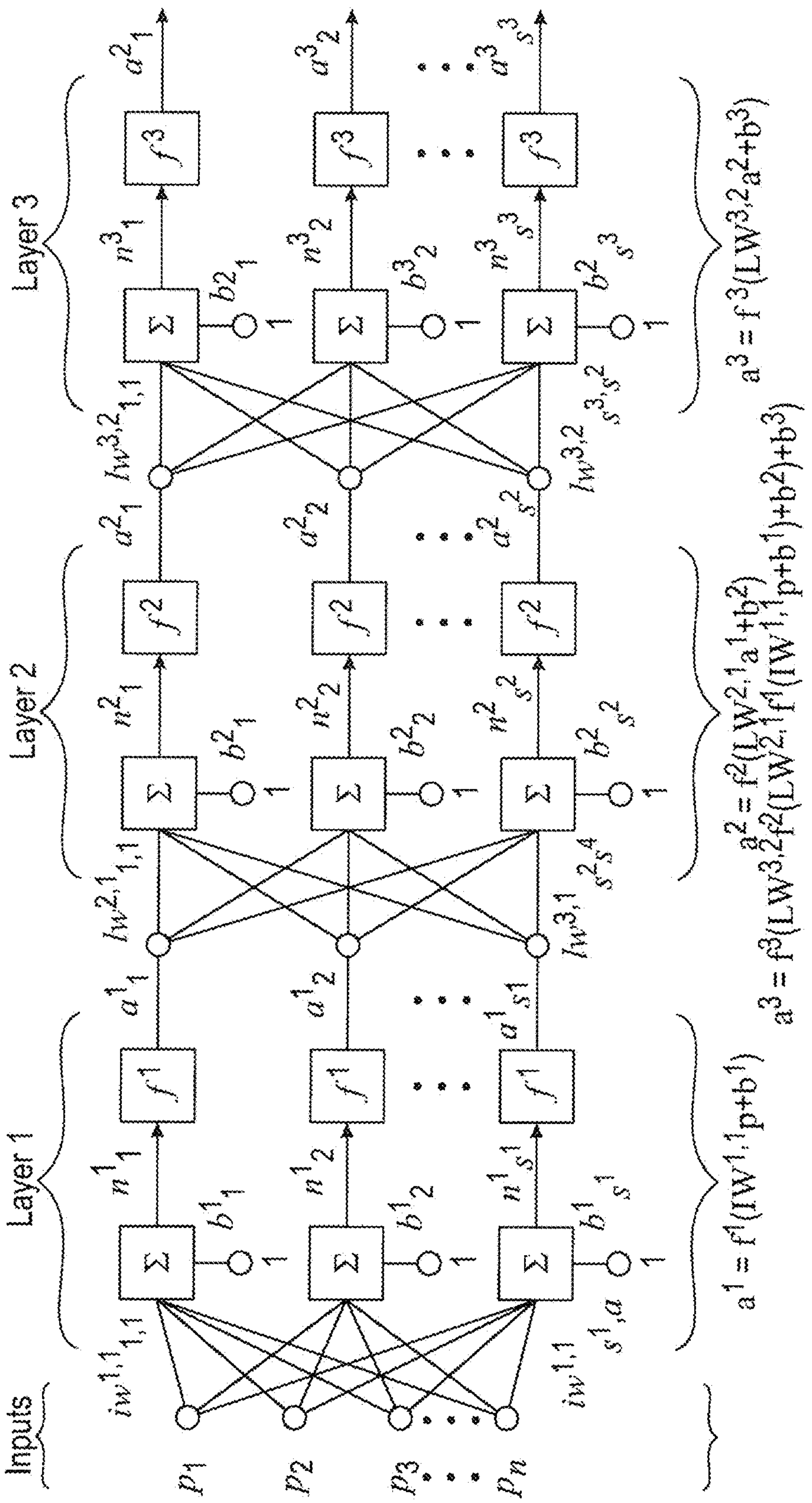
FIG. 22 shows an input layer and three inner layers to illustrate the increasing complexity of neural networks as the number of layers and neurons is increased.

FIGS. 19-23 illustrate aspects of neural networks. FIG. 19 shows a simple neuron. It has an input, p, to which is applied a weight, w (by multiplying). The result is then shown to a decision function, which outputs a value a. It is possible to also influence the neural by applying a bias, b. The decision function (FIG. 20) is usually some type of logical function that either abruptly (discontinuity) or gently (continuous function) assigns a value to the output of a neuron. It can also be a correlation value. A neuron can be extended to consider numerous inputs and weightings. The output of this neuron can then become one of the inputs for a subsequent layer of neurons as shown in FIG. 21.

Eventually the network can grow quite complex (see FIG. 22) with a very large number possible of combinations and weightings producing the output results. What is important, however, is that neural networks are not cumbersome from an analog computational perspective because the learning function (which is one of a number of functions which crawls through each neuron to adjust its weighting to see if it is improving or making worse the overall networks correspondence to the desired and provided output vector for a given input vector) only requires maintenance of the instantaneous value, of each weighting which is then fed back into the system for further updating. Very little memory is required. Additionally, in an analog implementation all of the calculations occur in parallel.

Figure 23:
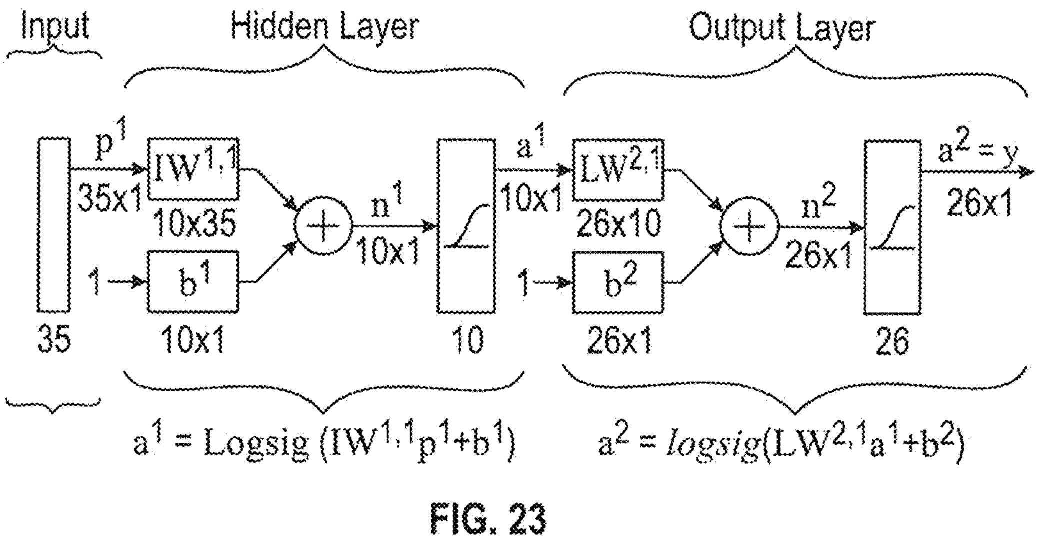
FIG. 23 shows a neural network sized to recognize the pattern of all of the letters of the alphabet even in a noisy environment to show the compactness of the method.

To see just how small such a neural network can be, consider a real pattern recognizing neural network in FIG. 23 that is used to learn and recognize the letters of the alphabet even if the pixels are of different intensity and difficult to see (ie. there is significant noise). The network has 35 input grayscale pixels, which are applied to ten weightings. These are in turn passed to a log sig function (the one shown in the description of the simple neuron of FIG. 20). The subsequent ten outputs are then passed to 26 weightings which are applied to another log sig function. The resulting output is a one in the position of the letter of the alphabet that the pixels represent as shown in 23 and zeros for all the other positions.

Figure 24:
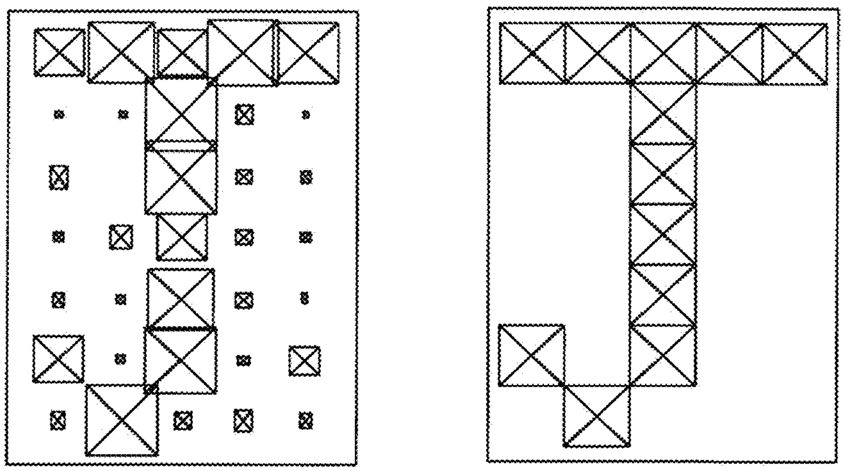
FIG. 24 shows an input vector for a character to be recognized including noise. If the pixels were turned into a vector of size 35 with each pixel a scale between 0-1 then the figure on the right is denoised (all 0's or 1's) while the figure on the left is noised (varying intensities between 0 and 1)
Figure 25:
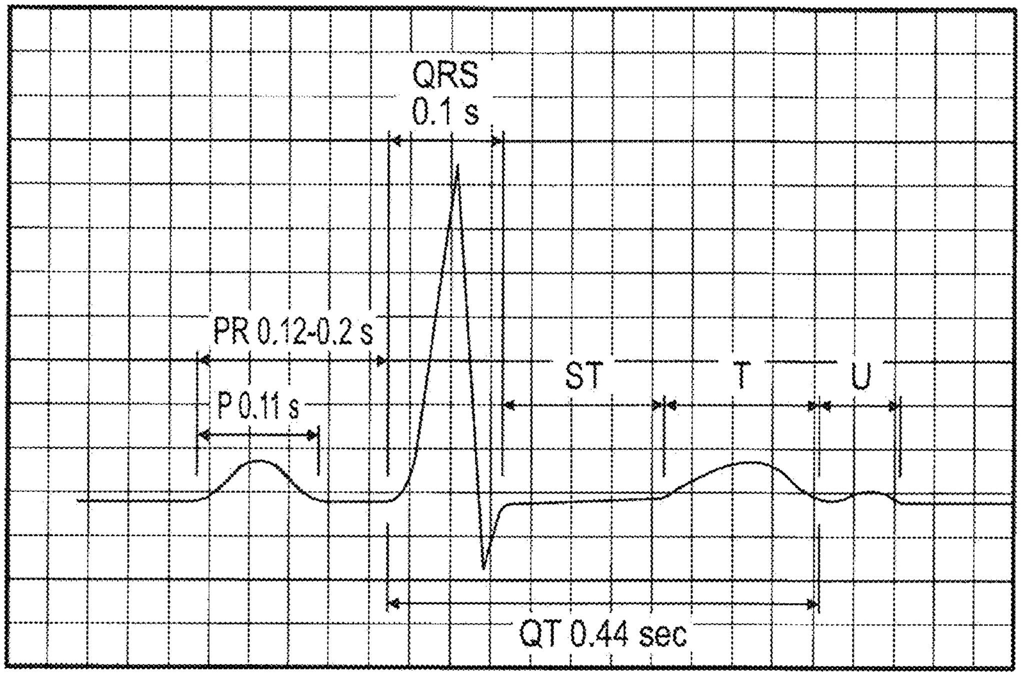
FIG. 25 illustrates the P, QRS, T complex.

The neural network of FIG. 23 is capable of recognizing both the noisy and distorted 'J' on the left or the 'J' it was "trained" to recognize on the right (FIG. 24) due to the flexibility of the neural algorithm. What is remarkable about the network just described is that it can recognize the entire alphabet with just 35 input bits, 36 weight storage floating point numbers, 10 inner layer floating point numbers, and 26 output bits. What also is interesting is that this size network can weight itself through a learning function to recognize all twenty six letters of the alphabet, not just one at a time! This example illustrates the power of neural networks to minimize the use of system resources while achieving astounding pattern recognition results.

In embodiments of the invention, rather than outputting one of 26 letters, the neural network indicates when a QRS complex is seen, and then the period between such recognitions is recorded. Thereafter the period is checked against rules known to be true about heart rate and heart rate variability (for example how quickly it can change) as well as the nature of the discontinuities or possible variation (do they look like electrode disconnect). If there is a recognized non-ideality like electrode disconnection, the neural network can make an attempt to use prediction to help fill in and see if the gaps fit, and finally drop problematic areas and data which do not conform to reasonable heart rates and repeat previous outputs for example to fill in the gaps. To output a simple heart rate is relatively simple using these techniques.

Now consider a training input vector subset containing at least one continuous heart beat waveform or which contains a waveform that might be mistaken for a heart beat signal or which contains waveform which is not heart beat signal. We may apply various transforms to this vector subset, such as filters, Hilbert function, correlation functions or other mathematical methods to highlight certain aspects of a heart rate signal to create additional subset vectors and/or we may simply utilize the original vector. We then create supersubset by concatenating multiple of these subsets from all these different transformations together in addition to the non-transformed subset. This vector may be created by utilizing information from a heart beat data bank, or by utilizing data from a subject during different types of activity.

The input vector supersubset above may now be transformed into a wavelet input vector supersubset by creating a three dimensional image using wavelet deconstruction on the supersubset. Additionally, certain of the wavelet components known to be outside the components of interest for a heart rate waveform or which resonate weakly with the custom wavelet may be removed to reduce computing overhead.

We now create the overall input vector by concatenating wavelet supersubsets together. Next we define an output vector of length equal to the number of concatenated supersubsets. The output vector will contain a '1' in each serial, position where the supersubset in the same serial position in the input vector contains a heart beat and a zero where it does not. A pattern recognizing neural network may now be trained utilizing said input and output vectors utilizing an error minimization function.

Thereafter said trained neural network may be utilized by applying wavelet supersubsets created from subset data extracted from incoming data from real world sensors, where said wavelet supersubsets are created by transforming subsets to create exactly the same type of input vector that we used to create the learning input vector. By applying said input vector to said neural network previously trained by said learning wavelet supersubsets, and finally examining the output vector to find the position of recognized heart beat components, we have a system which can recognize heart beats from noisy incoming data. This information may then be utilized to identify the areas in which heart beats reside and the heart beats may be reconstructed from wavelet components or utilizing other means to extract the heart beat waveform once their location is known. Alternatively, the recognition vector may be utilized to generate a heart rate for lower end devices. This method may be utilized either as a post processing methodology or as part of the algorithm which optimizes the waveform being allowed through the first stage of the INA as part of the AGC algorithm. In either case yet another error minimizing function may be utilized to alter such parameters such as neural network thresholding, which mathematical transforms or even which neural networks to be selected if more than one are used, to make flow branch decisions such as to take a resultant image and apply it to a clustering algorithm, or to perform other optimizations against a measure of output quality for each result.

Continuing now with the wavelet discussion, a wavelet neural network will be described. In the above examples, a neural network with a simple log sig (a soft digital '1' or '0') can be used to create a pattern recognition algorithm that is low on computing requirements and memory. Now consider a neural network whose input vector contains more complex weighted data coming in such as the results of various transforms applied to segments of the input waveform. Now instead of using log sig or some other function to create a single neuron output coefficient, consider instead utilizing a wavelet decomposition to produce an image at each neuron such that an error minimizing function can determine an overall correlation factor to the image (for example maximum rms difference of highlights vs. background) during training. The image is then passed to the next hidden layer which performs another type of analysis such as a clustering analysis and again an correlation factor for the image is determined (such as cluster spacing uniformity and highlight vs. background). It is possible to build a powerful computing engine that can utilize wavelets and a variety of transforms, pattern recognition techniques, and neural techniques to produce a error minimization methodology that may be used to isolate difficult to discern patterns;

An additional function of a neural network involved in pattern recognition is prediction. It may be imagined that the neural network can be extended to expect a certain input over time such that it may be used to produce a similar output. This property allows for "fill in the deadbands" where needed to complete a waveform. In other words, the neural network is able to create the missing data in some cases for the areas in the subject data that are of poor quality utilizing the neural networks predictive properties to allow a more continuous result. Although this is not critical for simple heart rate extraction, it is useful to output a full but partially reconstructed QRS heart beat dataset. For example if the neural network described earlier consistently found beats at a certain frequency, and a thresholding algorithm within the AGC suggested certain components corresponded to those heart beat locations, then the wavelet components could be "pasted" into the area predicted by the neural network to reconstruct the signal if we lose contact with the sensor or receive an unexpected recognition result.

It is noted that the network used for adaptive gain control (AGC), was a quicker, simpler neural network utilizing wavelet data and is different to the algorithm that is used for complex identification and prediction. The first algorithm can be created utilizing very low currents and analog techniques. The second algorithm can also be created in such a way, however, at present it is recommended that the AGC algorithm be on the integrated circuit (IC), and the more complex analysis be done in the cloud (i.e., remote server).

Appendix A is a discussion on the admissibility requirements for a wavelet and is incorporated in its entirety in this specification.

The invention has been described in an illustrative manner. It is, therefore, to be understood that the terminology used is intended to be in the nature of words of description rather than of limitation. Many modifications and variations of the invention are possible in light of the above teachings. Thus, within the scope of the appended claims, the invention may be practiced other than as specifically described.

Patent documents and publications mentioned in the specification are indicative of the levels of those skilled in the art to which the invention pertains. These documents and publications are incorporated herein by reference to the same extent as if each individual document or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

APPENDIX A

Admissibility Condition on a Wavelet

Continuous wavelet transform (CWT) of a function x(t) w.r.t. ψ(t) is given by:

$$WT_\psi\{x;b,a\} = C \int x(t)\overline{\psi\left(\frac{t-b}{a}\right)} dt$$

where, a and b are dilation and translation parameters and C is the normalizing factor such that, $$C\int \left|\psi\left(\frac{t-b}{a}\right)\right|^2 dt \text{ has unit engery}$$

$$\Rightarrow C = \frac{1}{\sqrt{a}}$$

Hence the CWT is expressed as:

$$W_\psi x(b,a) = \frac{1}{\sqrt{a}} \int x(t)\overline{\psi\left(\frac{t-b}{a}\right)} dt$$

Theorem:

The wavelet transform obeys a Parseval theorem like relationship.

$$\int\int W_\psi x(b,a)\overline{W_\psi y(b,a)} db \frac{da}{a^2} = C_\psi \int x(t)\overline{y(t)} dt$$

Proof:

First let us consider the single integral of LHS with w.r.t. b which can be transformed to w-Domain as:

$$\int W_\psi x(b,a)\overline{W_\psi y(b,a)} db = \frac{1}{2\Pi} \int W_\psi \hat{x}(b,a)\overline{W_\psi \hat{y}(b,a)} d\omega \quad (1)$$

which is defined as $$W_\psi \hat{x}(b,a) = \frac{1}{\sqrt{a}} \int x(t)\overline{\hat{\psi}\left(\frac{t-b}{a}\right)} dt$$

i.e. Transformation w.r.t b:

$$= \frac{1}{\sqrt{a}} \int e^{-j\omega b}\left\{\int x(t)\overline{\psi\left(\frac{t-b}{a}\right)} dt\right\} db$$

Exchanging db and dt;

$$= \frac{1}{\sqrt{a}} \int x(t)\left\{\int \overline{\psi\left(\frac{t-b}{a}\right)} e^{-j\omega b} db\right\} dt \quad (2)$$

Substitute $$\lambda = \frac{t-b}{a};$$

t=aλ+b; db=−adλ in $$\overline{\int \psi\left(\frac{t-b}{a}\right) e^{-j\omega b} db}$$

to get $$= |a| \overline{\int \psi(\lambda) e^{-j\omega(t-a\lambda)}} \tag{3}$$

$$= |a| \overline{\int \psi(\lambda) e^{-j\omega(t-a\lambda)}}$$

$$= |a| e^{-j\omega} \overline{\int \psi(\lambda) e^{-j\omega a\lambda}}$$

$$= |a| e^{-j\omega t} \overline{\psi(\hat{a}\omega)}$$

Substituting (3) back in (2)

$$\therefore W_\psi \hat{x}(b, a) = \frac{1}{|a|^{\frac{1}{2}}} \int x(t)\{|a| e^{-j\omega t} \overline{\psi(\hat{a}\omega)}\} dt \tag{4}$$

$$= |a|^{\frac{1}{2}} \left\{ \int x(t) e^{-j\omega t} dt \right\} \overline{\psi(\hat{a}\,\omega)}$$

$$= |a|^{\frac{1}{2}} \hat{x}(\omega) \overline{\psi(\hat{a}\omega)}$$

Substituting (4) back in (1)

$$\therefore \int W_\psi x(b, a) \overline{W_\psi y(b, a)} db = \frac{1}{2\Pi} \int \{|a|^{1/2} \hat{x}(\omega) \overline{\psi(\hat{a}\omega)}\} \overline{\{|a|^{1/2} \hat{y}(\omega) \overline{\psi(\hat{a}\omega)}\}} d\omega \tag{5}$$

$$= \frac{1}{2\Pi} \int |a| \hat{x}(\omega) \overline{\hat{y}(\omega)} |\psi(\hat{a}\omega)|^2 d\omega$$

$$\therefore LHS = \int\int W_\psi x(b, a) \overline{W_\psi y(b, a)} db \frac{da}{a^2}$$

$$= \frac{1}{2\Pi} \int\int \{|a| \hat{x}(\omega) \overline{\hat{y}(\omega)}\} \left|\hat{\psi}(a\omega)\right|^2 d\omega \frac{da}{a^2}$$

$$= \frac{1}{2\Pi} \int\int \hat{x}(\omega) \overline{\hat{y}(\omega)} \left\{ |\psi(\hat{a}\omega)|^2 \frac{da}{|a|} \right\} d\omega$$

Substituting aw=λ; we get $$\frac{da}{a} = \frac{d\lambda}{\lambda}$$

and $$\int\int W_\psi x(b, a) \overline{W_\psi y(b, a)} db \frac{da}{a^2} = \frac{1}{2\Pi} \left\{ \int \hat{x}(\omega) \overline{\hat{y}(\omega)} d\omega \right\} \left\{ \int \left|\hat{\psi}(\lambda)\right|^2 \frac{d\lambda}{\lambda} \right\}$$

for the RHS of the above integral to converge $$\int_0^\infty \left|\hat{\psi}(\lambda)\right|^2 \frac{d\lambda}{\lambda}$$

must converge say to a positive finite constant $$C_\psi => LHS = C_\psi \left\{ \frac{1}{2\Pi} \int \hat{x}(\omega) \overline{\hat{y}(\omega)} d\omega \right\} = C_\psi \int x(t) \overline{y(t)} dt \ (RHS)$$

(Using Parseval's Theorem)

Hence Proved

Example

Checking Admissibility Condition for Haar MRA:

Expression for Haar wavelet:

$$\left|\hat{\psi}(\omega)\right| = \left| \frac{\sin^2 \omega/4}{\omega/4} \right|$$

Applying admissibility condition:

$$\int_0^\infty \left|\hat{\psi}(\omega)\right|^2 \frac{d\omega}{\omega} = \int_0^\infty \frac{\sin^4(\omega/4)}{(\omega/4)^2} \frac{d\omega}{\omega}$$

The integral can be expressed as:

$$\int_0^\infty = \int_0^\partial + \int_\partial^\infty$$

For integral $$\int_0^\partial \left| \frac{\sin^2 \lambda/4}{\lambda/4} \right|^2 \frac{d\lambda}{\lambda} \le \int_0^\infty |\lambda/4|^2 \frac{d\lambda}{\lambda} = \int_0^\infty \frac{\lambda}{16} d\lambda (\because \sin\lambda \le \lambda)$$

which converges as ∂→0.

Also the integral $$\int_\partial^\infty \left| \frac{\sin^2 \lambda/4}{\lambda/4} \right|^2 \frac{d\lambda}{\lambda} < \int_\partial^\infty \frac{16}{\lambda^3}$$

(∵ sin λ<1) therefore as ∂→∞ the integral converges.

Hence Haar wavelet satisfies admissibility condition.

Inverse Continuous Wavelet Transform (ICWT)

From Parseval theorem, to get inverse wavelet transform choose y(t) to be an unit area narrow pulse around $t=t_0$ (or as impulse)

$$x(t_0) = K_\psi \int\int W_\psi x(b, a) \psi\left(\frac{t_0 - b}{a}\right) \frac{db\,da}{a^2}$$

where again $$K_\psi = \int |\hat{\psi}(\lambda)|^2 \frac{d\lambda}{\lambda};$$

a constant on the condition that $$\int |\hat{\psi}(\omega)|^2 \frac{d\omega}{\omega}$$

converges i.e. ADMISSIBILITY CONDITION.

It is because of admissibility, that the CWT is invertible.

If spectrum of $\psi(t)$ i.e. $\hat{\psi}(\omega)$ does not →0 as ω→0, then $$\int |\hat{\psi}(\omega)|^2 \frac{d\omega}{\omega}$$

diverges.

Therefore $\hat{\psi}(\omega)$ must decay at least as fast as ω, which says if ψ(.) is a band pass function then $$\int |\hat{\psi}(\omega)|^2 \frac{d\omega}{\omega}$$

converges.

The transform we have seen so far are redundant in nature. So now we go for discretization of scale and translation parameter.

1.1 Discretization of Scale Parameter a:

Consider $$\int |\hat{\psi}(\lambda)|^2 \frac{d\lambda}{\lambda}$$

Put $\lambda = e^{-v}$ $$\int_{-\infty}^{\infty} |\psi(-e^{-v})^2 dv$$

This quantity is Fourier transform of some autocorrelation sequence.

For $v \to v+v_0$; $e^v \to e^v e^{v_0}$ i.e. for uniform movement on v there is exponential movement in λ. This is logarithmic discretization. This means that the no. of points of discretization between a=1 and a=10 should be same as between a=10 and a=100 where 'a' is the scaling parameter.

Now choosing $a = a_0^m$ ($\infty > a_0 > 0$)

we get $$\int_0^{\infty} |\hat{\psi}(w)|^2 \frac{dw}{w} = \sum_{m=-\infty}^{+\infty} \int_{a_0^m}^{a_0^{m+1}} |\hat{\psi}(w)|^2 \frac{dw}{w}$$

now substituting $w = a_0^m \delta$;

$$\frac{dw}{w} = \frac{d\delta}{\delta}$$

we get:

$$= \sum_{m=-\infty}^{+\infty} \int_1^{a_0} |\hat{\psi}(a_0^m \delta)|^2 \frac{d\delta}{\delta}$$

taking the summation sign inside the integral we get:

$$= \int_1^{a_0} \left\{ \sum_{m=-\infty}^{+\infty} |\hat{\psi}(a_0^m \delta)|^2 \right\} \frac{d\delta}{\delta}$$

for this integral to converge;

$$0 < A \le \sum_{m=-\infty}^{+\infty} |\hat{\psi}(a_0^m \delta)|^2 \le B < \infty$$

i.e. strictly between 2 positive constants.

The bounded quantity is called the Sum of Dilated Spectra given by:

$$SDS(\psi, a_0)(\lambda) = \sum_{m=-\infty}^{+\infty} |\hat{\psi}(a_0^m \delta)|^2$$

and the condition of bounding is referred as Frame Property (it is also a check for possibility of inversion).

Wavelet Transform on function x(t) is given by $$W_\psi x(b, a) = \frac{1}{\sqrt{a}} \int x(t) \overline{\psi\left(\frac{t-b}{a}\right)} dt$$

Define $$g(t) = \frac{1}{\sqrt{a}} \overline{\psi\left(\frac{-t}{a}\right)}$$

$$g(b-t) = \frac{1}{\sqrt{a}} \overline{\psi\left(\frac{t-b}{a}\right)}$$

$$= \int x(t) g(b-t) dt$$

This is convolution of x(t) with g(.−t). So we can interpret wavelet transform as a linear filtering operation.

Frequency response of the LSI filter $$\hat{g}(w) = \int g(t) e^{-jwt} dt$$

-continued $$= \frac{1}{\sqrt{a}} \int \overline{\psi\left(\frac{-t}{a}\right)} e^{-jwt} dt \text{ Put } \frac{-t}{a} = \lambda$$

$$= \frac{1}{\sqrt{a}} \int \overline{\psi(\lambda)} e^{-jw(-a\lambda)} - a d\lambda$$

$$= -\sqrt{a} \int \overline{\psi(\lambda) e^{-j(aw)\lambda}} d\lambda$$

$$\therefore \hat{g}(w) = -\sqrt{a}\, \overline{\hat{\psi}(aw)}$$

That is we are filtering x(t).

ψ(t) is band-pass function and $\sqrt{a}\overline{\hat{\psi}(aw)}$ is a band-pass filter with center frequency $W_\psi/a$.

In this way the signal x(t) is filtered by different filters with different scale parameter.

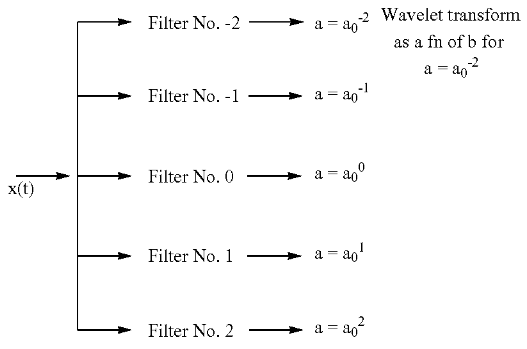

Similarly it can be shown that inverse wavelet transform is also a filtering operation.

Freq. domain output of $m^{th}$ filter at analysis side is $$=\hat{x}(w)\overline{\hat{\psi}(a_0^m w)} \text{ where } a_0>1$$

Output of $m^{th}$ synthesis filter $$=\hat{x}(w)\overline{\hat{\psi}(a_0^m w)}\hat{\psi}(a_0^m w)$$

$$=\hat{x}(w)|\hat{\psi}(a_0^m w)|^2$$

Output of the synthesis filter bank.

$$= \sum_m \hat{x}(w)|\psi(a_0^m w)|^2$$

$$= \hat{x}(w)\sum_m |\psi(a_0^m w)|^2$$

Therefore for perfect reconstruction (i.e. synthesis filter bank output=a multiple of the analysis filter bank input). i.e. $_m\Sigma|\psi(a_0{}^m w)|^2=C_1$ for all w.

The term $_m\Sigma|\psi(a_0{}^m w)|^2$, sum of dilated spectra $SDS_\psi$ should be a constant value. If $0<A\leq{}_m\Sigma|\psi(a_0{}^m w)|^2\leq B<\infty$ is true we can use different analysis and synthesis filter.

Also we can scale $\hat{\hat{\psi}}(w)$ such that $SDS(\tilde{\psi}, a_0)(w)=1$ which is given by $$\hat{\hat{\psi}}(w) = \frac{\hat{\psi}(w)}{+\sqrt{SDS(\psi, a_0)(w)}}$$

to get normalized bank of filters.

The invention claimed is:

1. A heart rate measurement device comprising:

a wavelet template;

an instrumentation amplifier;

a set of two electrodes configured to be coupled to a subject's skin, and in electrical communication with and providing a set of signals to said instrumentation amplifier;

an adaptive gain control (AGC) algorithm;

an analog or digital filter in a feedback path of said instrumentation amplifier for at least one of removal of saturating signals and unwanted waveform components responsive to said AGC algorithm;

wherein said AGC algorithm utilizes said wavelet template and responds to the correlation of said wavelet template to a measured signal obtained from said set of signals by said instrumentation amplifier; and wherein said device is configured to capture said set of signals utilizing a high common-mode resection ratio (CMRR) termination, which does not include a DC path to ground or overload said electrodes.

2. The device of claim 1 wherein said instrumentation amplifier further comprises:

two input amplifiers, where a level of gain is set by at least one of a variable resistor or impedance between the two input amplifiers, as well by feedback components around the two input amplifiers; and a summing amplifier.

3. The device of claim 1 wherein said instrumentation amplifier includes a common mode driver, a common mode accelerator, and an active feedback network.

4. The device of claim 1 wherein said instrumentation amplifier is configured for baseline capture by changing a set of feedback components such that saturation recovery is accelerated.

5. The device of claim 4 wherein the baseline capture is obtained with a third electrode driven to create a baseline between said set of signals from said two electrodes placed a minimum impedance away from each other.

6. The device of claim 1 wherein said measured signal is sent wirelessly to the cloud or a remote server for digital processing.

7. The device of claim 1 wherein said instrumentation amplifier precedes a hardware bessel filter.

8. The device of claim 1 wherein said measured signal is analyzed by a wavelet decomposition that builds up a three or more dimensional image of said measured signal.

9. The device of claim 8 wherein said three or more dimensional image is analyzed with pattern recognition methods to determine heart beat components responsive to a training algorithm.

10. The device of claim 9 wherein said pattern recognition methods are a neural network trained to recognize heart beat components from said measured signal.

11. The device of claim 10 wherein a periodic loss of signal is recovered through a prediction based on said neural network, where a rate or waveform may be reconstructed from discontinuous snapshots of heart beat trains.

12. The device of claim 1 wherein said wavelet is in resonance with one or more of the P, QRS and/or T reference components of a heart beat signal.

13. The device of claim 12 wherein said wavelet is configured to meet the following:

transform and inverse transform and decomposition requirements;

admissibility requirements including meeting the Perceval theorem condition; and convergence admissibility conditions.

14. The device of claim 1 further comprising a thresholding algorithm utilizing an error minimization algorithm to iteratively hunt for an optimal wavelet correlation to a train of heart beats.

15. The device of claim 14 further comprising an error minimization algorithm, wherein said error minimization algorithm thresholds the decomposition of a set of 2^n wavelet coefficients and one of optimizes relevant components or minimizes or removes any components of said set of signals which saturate said instrumentation amplifier and are unrelated to said heart rate signal by thresholding only relevant wavelet coefficients from said signal in a path of said digital filter;

wherein removed components comprise at least one of 60 Hz noise, muscle movement, electrode connection and misconnection, electromagnetic machine noise, respiration, motion artifacts, or other interference sources.

16. The device of claim 2 wherein said instrumentation amplifier comprises at least one of two digital or two neural network formed transfer functions replacing said two input amplifiers and feedback components in the first stage, where a gain and selection of waveform components to pass through said transfer functions are set in conformance with an AGC algorithm.

17. The device of claim 16 wherein said AGC algorithm includes a wavelet decomposition and error minimization function such that only those wavelet decomposition components responsive to a heart rate waveform are allowed through said first stage of said instrumentation amplifier.

18. A method for conditioning a measured signal of a heart rate measurement device comprising:

providing a heart rate measurement device comprising:

a wavelet template;

an instrumentation amplifier;

a set of two electrodes configured to be coupled to a subject's skin, and in electrical communication with and providing a set of signals to said instrumentation amplifier;

an adaptive gain control (AGC) algorithm;

an analog or digital filter in a feedback path of said instrumentation amplifier for at least one of removal of saturating signals and unwanted waveform components responsive to said AGC algorithm;

wherein said AGC algorithm utilizes said wavelet template and responds to the correlation of said wavelet template to a measured signal obtained from said set of signals by said instrumentation amplifier; and wherein said device is configured to capture said set of signals utilizing a high common-mode rejection ratio (CMRR) termination, which does not include a DC path to ground or overload said electrodes;

removing artifacts outside a heart rate window by applying one or more Bessel filters to create filtered waveform;

smoothing said filtered waveform with a smoothing function by averaging points around each point to create a baseline;

subtracting the baseline from the filtered waveform; and performing adaptive gain control (AGC) on the filtered signal in conformance with a three or more dimensional image produced using iterative decomposition wavelet template algorithm.

19. A method of heart waveform extraction comprising:

providing a wavelet template responsive to PQRST components of said heart waveform;

providing a contaminated signal containing said heart waveform as well non-ideal components measured by set of two electrodes configured to be coupled to a subject's skin;

using a processor to provide an at least three dimensional image created by deconstructing said contaminated signal utilizing said wavelet template by said processor; and providing a pattern recognition neural network trained to recognize heart beat components from an image created from similar wavelet deconstructed signals including noise components, wherein said at least three dimensional image is applied to said neural network trained to produce an output vector responsive to recognized heart beats.

20. A heart rate measurement device comprising:

a wavelet;

an instrumentation amplifier;

a set of two electrodes configured to be coupled to a subject's skin, and in electrical communication with and providing a set of signals to said instrumentation amplifier;

an adaptive gain control (AGC) algorithm;

an analog or digital filter in a feedback path of said instrumentation amplifier for at least one of removal of saturating signals and unwanted waveform components responsive to said AGC algorithm;

wherein said AGC algorithm utilizes said wavelet and responds to the correlation of said wavelet to a measured signal obtained from said set of signals by said instrumentation amplifier;

wherein said measured signal is analyzed by a wavelet decomposition that builds up a three or more dimensional image of said measured signal, said three or more dimensional image analyzed with pattern recognition methods to determine heart beat components responsive to a training algorithm; and wherein said pattern recognition methods are a neural network trained to recognize heart beat components from said measured signal.

* * * * *